(12) United States Patent
Kim et al.

(10) Patent No.: US 7,904,142 B2
(45) Date of Patent: Mar. 8, 2011

(54) SELF-ADJUSTING ECG MORPHOLOGICAL FEATURE CORRELATION THRESHOLD

(75) Inventors: Jaeho Kim, Redmond, WA (US);
Joseph M. Bocek, Seattle, WA (US);
Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 947 days.

(21) Appl. No.: 11/749,283

(22) Filed: May 16, 2007

(65) Prior Publication Data

US 2008/0288009 A1    Nov. 20, 2008

(51) Int. Cl.
*A61B 5/0402* (2006.01)

(52) U.S. Cl. ........................................ 600/515
(58) Field of Classification Search .................. 600/515
See application file for complete search history.

(56) References Cited

U.S. PATENT DOCUMENTS

| | | | |
|---|---|---|---|
| 2004/0093035 A1* | 5/2004 | Schwartz et al. | 607/5 |
| 2005/0149125 A1* | 7/2005 | Kim et al. | 607/5 |
| 2006/0217621 A1 | 9/2006 | Kim et al. | |

OTHER PUBLICATIONS

Gold, M., et al., "Rhythm Discrimination Using a New Electrogram Vector Timing and Correlation (VTC) Algorithm", *NASPE 2001*, PowerPoint Presentation, (2001).

Kim, Jaeho, et al., "Rhythm Discrimination of Sudden Onset and One-to-One Tachyarrhythmia", U.S. Appl. No. 11/276,213, filed Feb. 17, 2006, 33 Pages.

Kim, Jaeho, et al., "Tachyarrhythmia Sudden Onset Detection With Hysteresis", U.S. Appl. No. 11/301,440, filed Dec. 13, 2005, 22 Pages.

Kim, Jaeho, et al., "Zoneless Tachyarrhythmia Detection With Real-Time Rhythm Monitoring", U.S. Appl. No. 11/301,716, filed Dec. 13, 2005, 41 Pages.

\* cited by examiner

*Primary Examiner* — Carl H Layno
*Assistant Examiner* — Paula J Stice
(74) *Attorney, Agent, or Firm* — Schwegman, Lundberg & Woessner, P.A.

(57) ABSTRACT

An apparatus comprising an implantable cardiac signal sensing circuit configured for sensing an intrinsic cardiac signal, a memory to store a template of a morphology of normal atrial-ventricular conduction, and a controller that includes a tachyarrhythmia detection circuit and a correlation circuit. The tachyarrhythmia detection circuit is configured for detecting a rhythm with elevated ventricular rate using the sensed intrinsic cardiac signal. The correlation circuit is configured for iteratively calculating a correlation between the sensed intrinsic cardiac signal and the template, and comparing the calculated correlation to a variable correlation threshold to determine whether the detected rhythm correlates to the template. The apparatus also includes a therapy circuit configured for inhibiting a ventricular tachycardia therapy when the detected rhythm correlates to the template. Other apparatuses and methods are described.

33 Claims, 16 Drawing Sheets

SELF-ADJUSTING ECG MORPHOLOGICAL FEATURE CORRELATION THRESHOLD

FIELD OF THE INVENTION

The field generally relates to implantable medical devices and, in particular, but not by way of limitation, systems, devices, and methods for detecting cardiac arrhythmia and providing anti-arrhythmia therapy to a subject.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring electrical heart activity signals. In CFM devices, these events include heart chamber expansions or contractions. By monitoring cardiac signals indicative of expansions or contractions, IMDs are able to detect tachyarrhythmia. IMDs are further able to provide therapy for tachyarrhythmia, such as high energy shock therapy or anti-tachycardia pacing (ATP). Tachyarrhythmia includes abnormally rapid heart rate, or tachycardia, including ventricular tachycardia (VT), supraventricular tachycardia (SVT), and sinus tachycardia (ST). Tachyarrhythmia also includes rapid and irregular heart rate, or fibrillation, including ventricular fibrillation (VF). Typically, ICDs detect tachyarrhythmia by first detecting a rapid heart rate. Other detection methods in addition to fast rate detection are used to reduce the incidence of inappropriate shocks. The present inventors have recognized a need for improved sensing of events related to device recognition of tachyarrhythmia.

SUMMARY

This document discusses, among other things, devices and methods for detecting events related to cardiac activity. A device example includes an implantable cardiac signal sensing circuit configured for sensing an intrinsic cardiac signal, a memory to store a template of a morphology of normal atrial-ventricular conduction, and a controller that includes a tachyarrhythmia detection circuit and a correlation circuit. The tachyarrhythmia detection circuit is configured for detecting a rhythm with elevated ventricular rate using the sensed intrinsic cardiac signal. The correlation circuit is configured for iteratively calculating a correlation between the sensed intrinsic cardiac signal and the template, and comparing the calculated correlation to a variable correlation threshold to determine whether the indicated rhythm correlates to the template. The device also includes a therapy circuit configured for inhibiting a ventricular tachycardia therapy when the detected rhythm correlates to the template.

A method example includes sensing an intrinsic cardiac signal, detecting a rhythm with elevated ventricular rate from the cardiac signal, calculating a correlation between at least one cardiac signal of the detected rhythm and a template, comparing the calculated correlation to a variable correlation threshold to determine whether the detected rhythm correlates to a rhythm for which a ventricular tachycardia (VT) therapy is contraindicated, and iteratively calculating the correlation and inhibiting the VT therapy while the detected tachyarrhythmia correlates to the template according to a comparison of the calculated correlation to the variable correlation threshold.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

Figure 1:
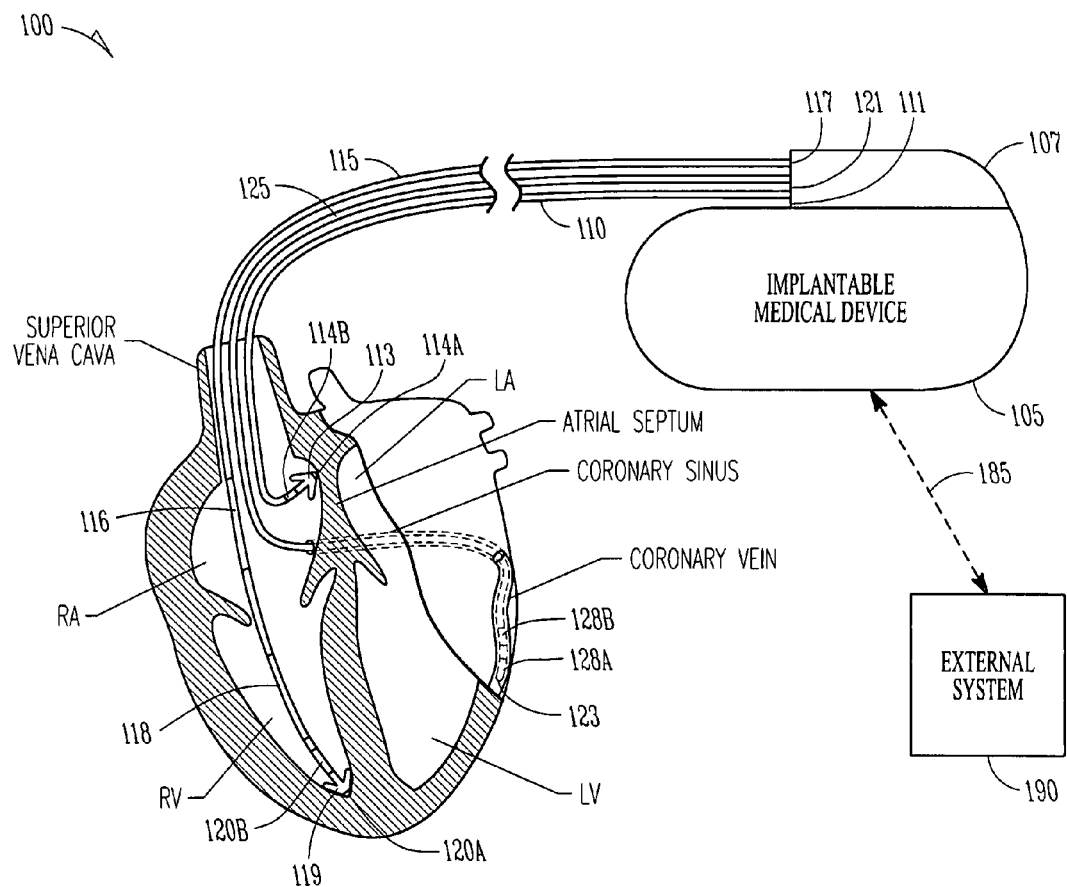
FIG. 1 is an illustration of portions of a system that uses an implantable medical device (IMD).

This document discusses systems and methods for improved detection of cardiac events. FIG. 1 is an illustration of portions of a system 100 that uses an implantable medical device (IMD) 105. Examples of IMD 105 include, without limitation, a, pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown can be used to treat a cardiac tachyarrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." System 100 also typically includes an IMD programmer or other external system 190 that communicates one or more wireless signals 185 with the IMD 105, such as by using radio frequency (RF) or one or more other telemetry signals.

The example shown includes right atrial (RA) lead 110 having a proximal end 111 and a distal end 113. Proximal end 111 is coupled to a header connector 107 of the IMD 105. Distal end 113 is configured for placement in the RA in or near the atrial septum. RA lead 110 may include a pair of bipolar electrodes, such as an RA tip electrode 114A and an RA ring electrode 114B. RA electrodes 114A and 114B are incorporated into the lead body at distal end 113 for placement in or near the atrial septum, and are each electrically coupled to IMD 105 through a conductor extending within the lead body. The RA lead is shown placed in or near the atrial septum, but the RA lead may be placed in the atrial appendage.

The example shown also includes right ventricular (RV) lead 115 having a proximal end 117 and a distal end 119. Proximal end 117 is coupled to header connector 107. Distal end 119 is configured for placement in the RV. RV lead 115 may include one or more of a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA or the superior vena cava. Defibrillation electrode 118 is incorporated into the lead body near distal end 119 for placement in the RV. RV electrodes 120A and 120B may form a bipolar electrode pair and are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or an electrode formed on the can of IMD 105 allow for delivery of cardioversion/defibrillation pulses to the heart.

RV tip electrode 120A, RV ring electrode 120B, and/or an electrode formed on the can of IMD 105 allow for sensing an RV electrogram indicative of RV depolarizations and delivering RV pacing pulses. RA tip electrode 114A, RA ring electrode 114B, and/or an electrode formed on the can of IMD 105 allow for sensing an RA electrogram indicative of RA depolarizations and delivering RA pacing pulses. Sensing and pacing allows the IMD 105 to adjust timing of the heart chamber contractions. In some device examples, IMD 105 can adjust the timing of ventricular contractions with respect to the timing of atrial contractions delay by sensing a contraction in the RA and pacing the RV at the desired atrial-ventricular (AV) delay time.

Also shown is a left ventricular (LV) lead 125. LV lead 125 is a coronary pacing and/or sensing lead that includes an elongate lead body having a proximal end 121 and a distal end 123. Proximal end 121 is coupled to header connector 107. Distal end 123 is configured for placement or insertion in the coronary vein. LV lead 125 may include an LV ring or tip electrode 128A and an LV ring electrode 128B. The distal portion of LV lead 125 is configured for placement in the coronary sinus and coronary vein such that LV electrodes 128A and 128B are placed in the coronary vein, LV electrodes 128A and 128B may form a bipolar electrode pair and are incorporated into the lead body at distal end 123 and each electrically coupled to IMD 105 through a conductor extending within the lead body. LV tip electrode 128A, LV ring electrode 128B, and/or an electrode formed on the can of IMD 105 allow for sensing an LV electrogram indicative of LV depolarizations and delivering LV pacing pulses.

Other forms of electrodes include meshes and patches, which may be applied to one or more portions of heart, or which may be implanted in one or more other areas of the body to help "steer" electrical current produced by IMD 105 in FIG. 1. The IMDs may be configured with a variety of electrode arrangements, including transvenous, endocardial, or epicardial electrodes (e.g., intrathoracic electrodes), or subcutaneous, non-intrathoracic electrodes, such as can, header, or indifferent electrodes, or subcutaneous array or lead electrodes (e.g., non-intrathoracic electrodes). Monitoring of electrical signals related to cardiac activity may provide early, if not immediate, diagnosis of cardiac disease.

ATP therapy regimens typically treat fast heart rates through short bursts of rapid pacing into either the atrium or ventricle (depending on where the fast heart rate is detected). In certain examples, an IMD can be programmed to provide ATP to any one of the RA, RV, LV, or any combination of the RA, RV, and LV. Additionally, various parameters related to a regimen of ATP therapy can be programmable. Examples of programmable parameters include, among other parameters, the number of bursts in an ATP therapy regimen, the number of pacing pulses in a burst of ATP, the amplitude of the pacing pulses, the pulse width of the pacing pulses, the time between bursts, and the time between pacing pulses in a burst. Other parameters can include a coupling interval and a timeout time duration. The coupling interval is the time between an abnormal rhythm depolarization and the first ATP pulse. For capture of the heart to be achieved and normal sinus rhythm (NSR) restored, it is preferable for the end of the coupling interval to occur when the ventricle is in a non-refractory state. When a timeout for the ATP therapy occurs without capture and NSR restoration, the CFM device can change over to delivering a high-energy shock therapy.

Figure 2A:
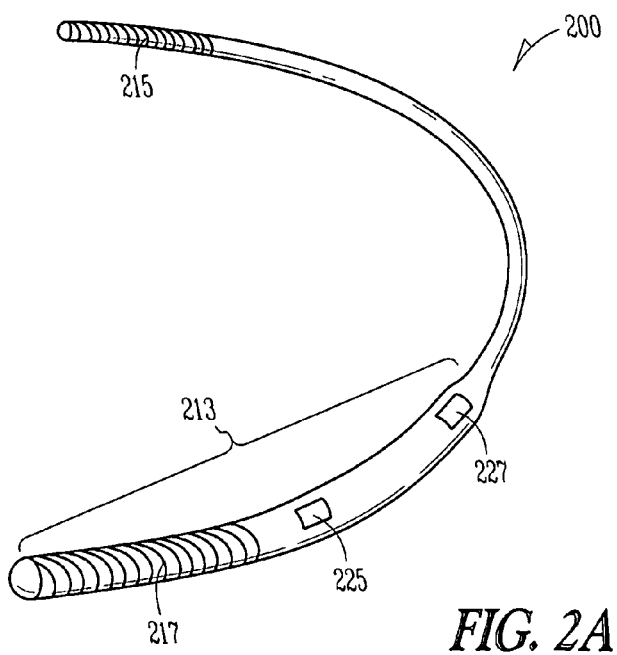
FIGS. 2A-B show an example of an IMD that does not use intravascular leads to sense cardiac signals.
Figure 2B:
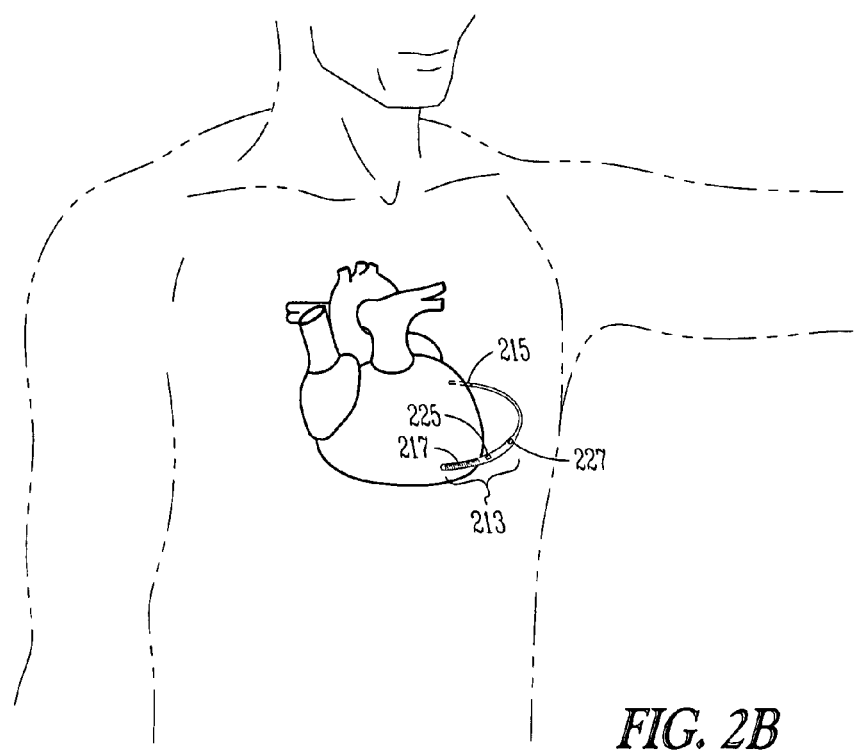

The present methods and systems will work in a variety of configurations and with a variety of electrodes. FIGS. 2A-B show an example of an IMD 200 that does not use intravascular leads to sense cardiac signals. FIG. 2A shows an example in which the IMD 200 includes a thicker end 213 to hold the power source and circuits. In this example, the IMD 200 also includes electrodes 225 and 227, such as for remote sensing of cardiac signals. Cardioversion/defibrillation can be provided through electrodes 215 and 217. FIG. 2B shows an example of the IMD 200 positioned within a patient. Monitoring electrical signals related to cardiac activity may provide early, if not immediate, diagnosis of cardiac disease.

Ventricular tachyarrhythmia can be terminated with high energy shock therapy using a CFM that includes cardioversion/defibrillation capability. However, cardioversion/defibrillation therapy can cause patient discomfort and can consume a relatively large amount of device battery power. Improved methods of rhythm detection and rhythm discrimination may reduce inappropriate delivery of the cardioversion/defibrillation shock therapy.

In some examples, discriminating between cardiac rhythms may include a combination of heart rate based tachyarrhythmia detection with morphology based tachyarrhythmia classification. Heart rate based tachyarrhythmia detection may include one or more measures of heart rate or rate interval, rate stability, and the ratio of ventricular to atrial rate (V:A). One or more of such measures can be compared to corresponding threshold values programmed into the device, such as to discriminate between the various types of tachyarrhythmia. Heart rate based tachyarrhythmia detection can also include detection of gradual or sudden tachyarrhythmia onset.

The morphology-based method typically compares the morphological shape of a cardiac depolarization to a template morphology, such as to classify a heart beat or heart rhythm. In the comparison, a correlation value can be determined (e.g., a feature correlation coefficient (FCC)) that can provide an indication of a degree of similarity between the shape of a depolarization being examined and the shape of the template to which it is compared. The correlation value can be compared to a correlation threshold value (e.g., $FCC_{th}$), such as to classify the rhythm as VT or SVT (e.g., ST, atrial fibrillation (AF), atrial flutter (AFL), or atrial tachyarrhythmia).

During an episode of SVT, the correlation value can recurrently become low—making it difficult to differentiate between the SVT and VT. If the morphology comparison is to a single correlation threshold, the low comparison value could cause unnecessary delivery of shock therapy during an episode of SVT. Also, during an episode of AF, the heart rhythm may become marginally uncorrelated to the template morphology. If the correlation threshold is set too high, an episode of AF could also result in unnecessary delivery of shock therapy. Therefore it can be desirable to use some other detection schema, such as a variable correlation threshold or more than one fixed correlation threshold, when classifying rhythms by correlation to a template rhythm.

Figure 3A:
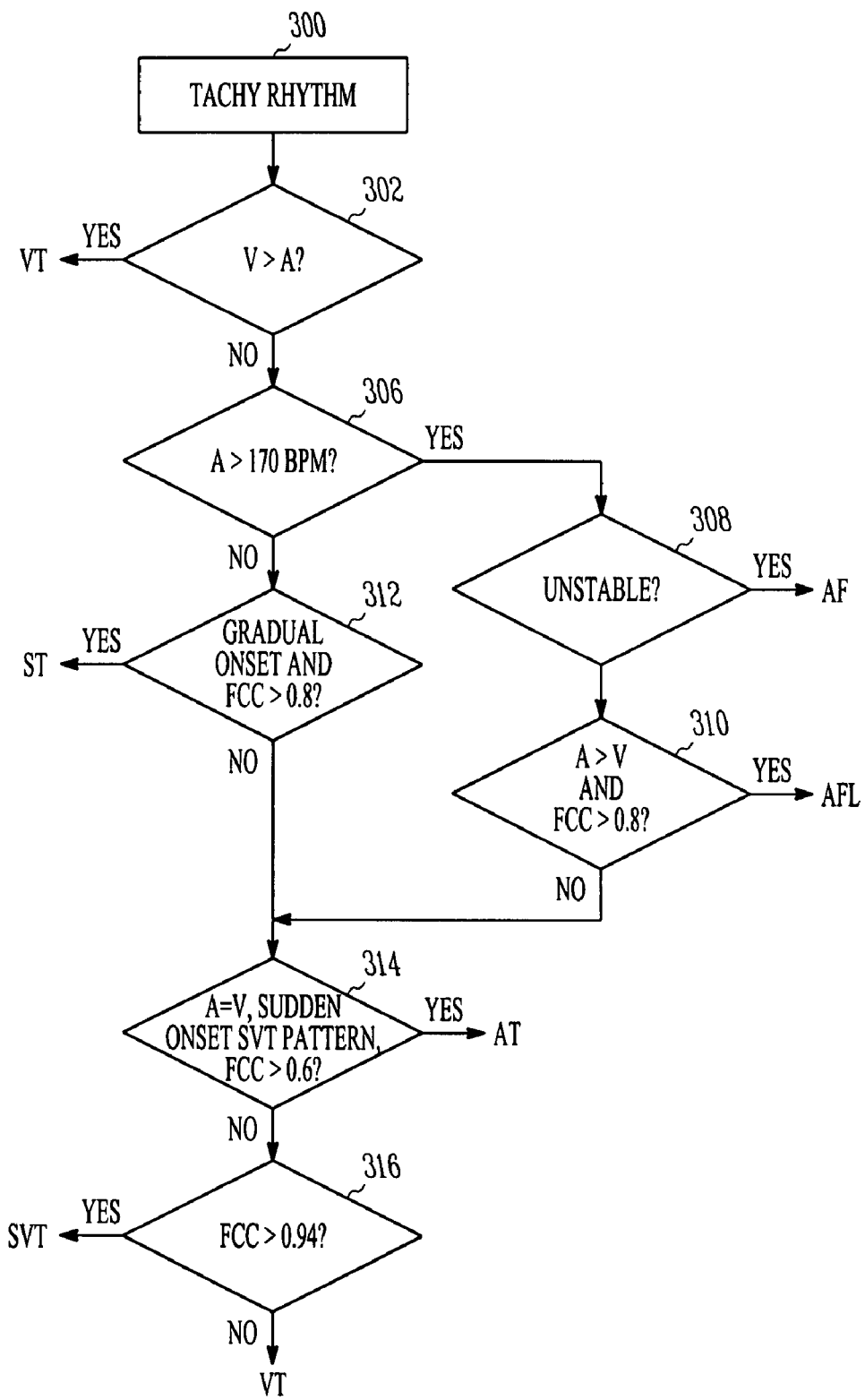
FIGS. 3A and 3B are flow diagrams of a method of abnormal cardiac rhythm classification.

FIG. 3A shows an example of a method of rhythm identification. At 300, a tachyarrhythmia is detected. In some examples, tachyarrhythmia is deemed detected when a detected heart rate exceeds a tachyarrhythmia rate threshold value. A device that includes an ICD may have multiple programmed tachyarrhythmia rate zones. Classification of the detected tachyarrhythmia, such as by discriminating between various possible heart rhythms, can also be performed.

At 302, a detected ventricular heart rate can be compared to a detected atrial heart rate. If the ventricular heart rate exceeds the atrial heart rate, then a ventricular tachycardia is declared. Otherwise, method flow continues at 306. At 306, the atrial heart rate is compared to an atrial rate threshold value. If the atrial heart rate exceeds a threshold value (e.g., 170 beats per minute), flow continues to 308 and 310 to determine whether the tachyarrhythmia represents atrial fibrillation (AF) or atrial flutter (AFL). Otherwise, at 306, if the atrial heart rate does not exceed the atrial rate threshold value, then the method flow continues at 312.

At 312, a determination can be made as to whether the detected tachyarrhythmia episode onset was sudden or gradual. In an illustrative example, sudden onset can be declared when two or more consecutive "fast" or accelerated beats are detected, where a "fast" beat can be defined as a beat that occurs at 10% faster than a windowed-average heart rate; otherwise a gradual onset can declared. Descriptions of detecting sudden rate onset and accelerated beats is found in Kim et al., U.S. patent application Ser. No. 11/301,716, filed Dec. 13, 2006, which is incorporated herein by reference.

The chances that tachyarrhythmia will be classified as ST can be adjusted by: (1) adjusting one or more of the criteria for distinguishing between sudden and gradual onset; (2) adjusting the feature correlation coefficient (FCC); or (3) both of the above. As an example, improved specificity to an ST indication can be accomplished by setting the FCC to a value lower than 0.94 and using at least one relaxed criteria for declaring gradual onset. Examples of relaxing the criteria for declaring gradual onset include increasing a number of fast beats necessary for sudden rate onset to be declared, or defining a fast beat as a higher percentage faster than a windowed-average heart beat. These examples make it more difficult for sudden onset to be declared and therefore easier for gradual onset to be declared.

At 312, if the tachyarrhythmia episode's onset was gradual, and if the FCC exceeds a more relaxed threshold (e.g., FCC>0.8), then a sinus tachyarrhythmia (ST) rhythm is declared. Otherwise, process flow continues to 314.

At 308, an assessment of the heart rate stability of the tachyarrhythmia episode is performed. Stability can be determined from the beat-to-beat variability in heart rate or depolarization intervals. If such a variability measurement exceeds a threshold value, the episode can be deemed unstable. If, at 308, the tachyarrhythmia episode is deemed unstable at 308, then AF is declared. If it is preferred to adopt a more strict approach to declaring AF, such as in view of known patient history, the stability threshold value can be increased. In either case, if stability is not met at 308, method flow continues to 310.

At 310, if the results of the previous atrial heart rate comparison to the ventricular heart rate (e.g., at 302) indicate that the atrial heart rate exceeds the ventricular heart rate (A>V), and if the FCC computed also exceeds a relaxed threshold (e.g., FCC>0.8), then AFL is declared. Similarly to 308 above, if it is desired to adjust the specificity of this AFL indication, the conditions may be adjusted or programmed accordingly. For example, to decrease the sensitivity of AFL indication, a larger threshold value can be imposed on the A>V rate difference determination, or the FCC threshold can be raised, such as to 0.94. In either case, if AFL is not indicated, process flow continues to 314, such as described above.

At 314, the results of (1) the previous atrial heart rate comparison to the ventricular heart rate (e.g., at 302), (2) the previous determination as to whether the tachyarrhythmia episode's onset was sudden or gradual (e.g., at 312), and (3) the comparison of the depolarization morphology to the SVT template (e.g., at 304) can be used. At 314, if the atrial heart rate correlates 1:1 with the ventricular heart rate, the tachyarrhythmia episode was a sudden onset with SVT onset pattern, and a more relaxed FCC threshold of 0.6 is exceeded, then AT is declared. One example in which a sudden onset exists includes the determination that two consecutive ventricular events occur between two consecutive atrial events (e.g., a pattern of AVVA occurs). Such a result can be considered as a VT onset pattern. Otherwise, it can be considered an SVT onset pattern. Descriptions of systems and methods to discriminate between a VT and SVT, such as upon detecting sudden onset and 1:1 tachycardia, are found in Kim et al., U.S. patent application Ser. No. 11/276,213, "Rhythm Discrimination of Sudden Onset and One-to-One Tachyarrhythmia," filed Feb. 17, 2006, which is incorporated herein by reference.

At 316, a morphology of one or more of the depolarizations in the detected tachyarrhythmia episode can be compared to a template morphology to compute a degree of similarity using a correlation value (e.g., FCC). If the calculated FCC exceeds a threshold FCC value (e.g., FCC>0.94), then a supraventricular tachyarrhythmia (SVT) can be declared. Otherwise, VT can be declared.

Figure 3B:
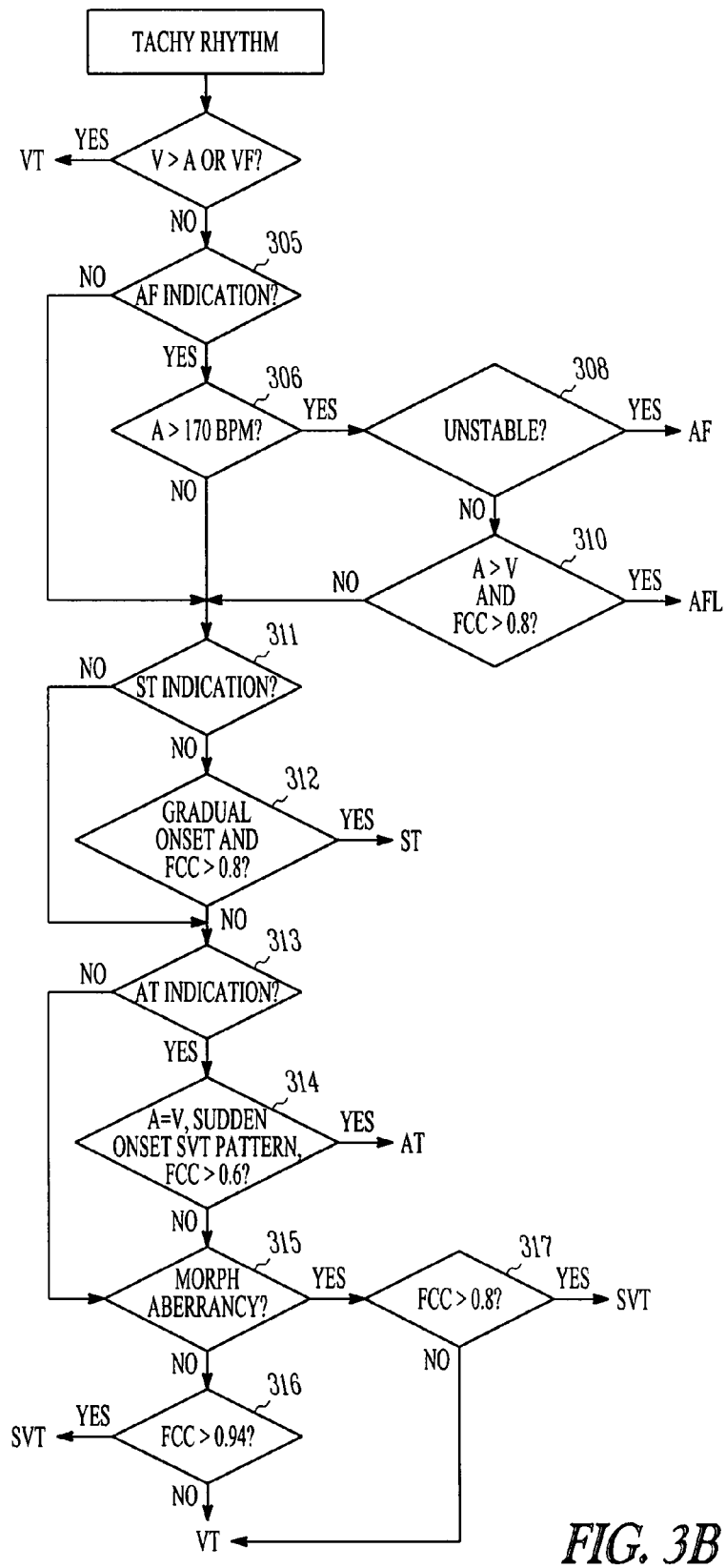

FIG. 3B shows another example of a method of rhythm identification. The method can be thought of as similar to the method of FIG. 3A, however, the check for a certain arrhythmia may be skipped or bypassed if the patient has no indication for that type of arrhythmia. For example, at 305, the checks for AF or AFL in 306, 308, and 310 are bypassed if the patient has no history of AF or AFL. Similarly, the check for ST at 312 may be bypassed if at 311 the patient has no indication of ST, such as if the patient's normal heart rate or sinus tachyarrhythmia rate never exceeds the ventricular tachyarrhythmia rate threshold, for example. At 313, if the patient has no history of AT, the check for AT of 314 can be bypassed.

In some cases a patient may tend to exhibit a rate dependent morphology aberrancy (e.g., conduction path changes as the heart rate increases). If so, then it may be desired to specify a different SVT indication for such a patient. For example, if the detected tachyarrhythmia rate is higher than a known aberrancy triggering rate, then the FCC threshold value can be lowered (e.g., 0.90), or a switch can be made to a non-morphology based detection method if the ventricular rate exceeds a rate threshold (or if a ventricular rate interval is less than an interval rate threshold). Values of the FCC during an episode of SVT may be low and therefore making it difficult to differentiate between SVT and VT.

At 315, if the patient has a history of morphology aberrancy, the FCC threshold can be lowered to 0.80. If the calculated FCC is greater than 0.80, SVT can be declared, otherwise VT can be declared. If the patient does not have a history of a morphology aberrancy, SVT can be declared if the calculated FCC is greater than 0.94. Otherwise, VT can be declared.

Figure 4:
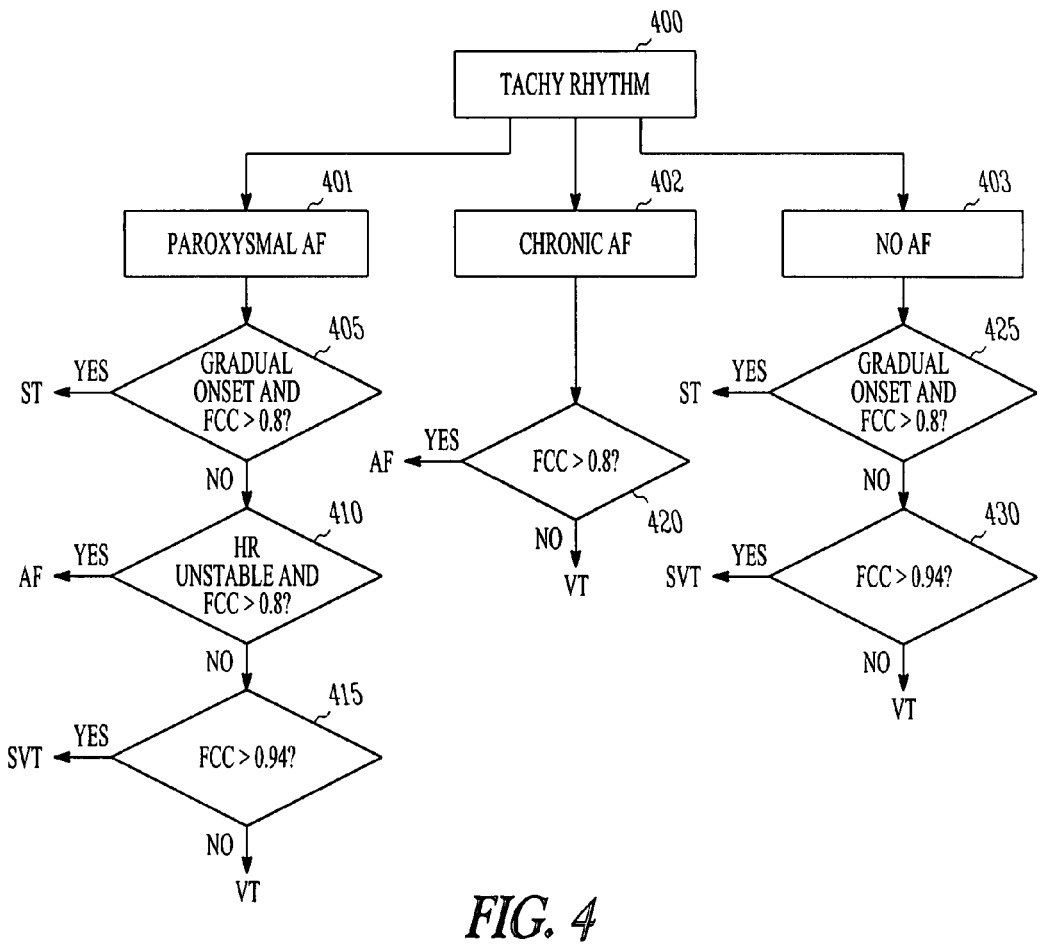
FIG. 4 is a flow diagram of another method of abnormal cardiac rhythm classification.

A system that includes rhythm identification (e.g., Rhythm ID™) of a single chamber ventricular channel device (VR device) can be modified in structure based upon the type of AF indication present. This modified structure may include one of the following techniques: (1) Paroxysmal AF indication, (2) Chronic AF indication, or (3) No AF indication. In the example of FIG. 4, at 400, a tachyarrhythmia is detected, such as by detecting a heart rate that exceeds a tachyarrhythmia rate threshold. Control may then branch into each of the three techniques.

Under a paroxysmal AF indication branch of 401, it can be determined at block 405 if the FCC exceeds a relaxed FCC setting of 0.8 and whether gradual onset is declared using at least one relaxed criterion. If both of these are met, ST can be indicated. Otherwise, at 410, if heart rate (HR) is unstable and the FCC exceeds 0.8, AF can be indicated, else flow continues at 415. At 415, if the FCC exceeds a value of 0.94, the rhythm can be classified as a SVT. Otherwise VT can be declared.

Under a chronic AF indication branch of 402, if the FCC exceeds a value of 0.8, the rhythm can be classified as an AF at 420. If not exceeding an FCC of 0.8, at 420, VT can be indicated. Under the no AF indication branch of 403, it can be determined whether the FCC exceeds a lower setting of 0.8 and whether gradual onset is declared. If, at 425, both of these conditions are met, ST can be indicated. At 430, if the FCC exceeds a value of 0.94, the rhythm can be classified as a SVT; otherwise, VT can be indicated.

Morphology based rhythm classification can be enhanced if the FCC threshold value self adjusts or "floats" rather than having one or more fixed values for the FCC threshold. Calculated values of FCC during an episode of SVT may be low and therefore making it difficult to differentiate between SVT and VT. Also, sometimes the calculation of FCC starts high, indicating a good correlation to the template rhythm, and then becomes low gradually. As an illustrative example, assume a tachyarrhythmia is detected that correlates to ST. While the ST rhythm continues and correlates to a template, therapy is inhibited. If the calculated FCC for the rhythm gradually becomes lower until it is deemed uncorrelated by a comparison to a fixed FCC threshold, shock therapy, such as cardioversion and/or defibrillation therapy, is initiated. However, because the rhythm was already a sinus rhythm, shock therapy is unnecessary.

Figure 5:
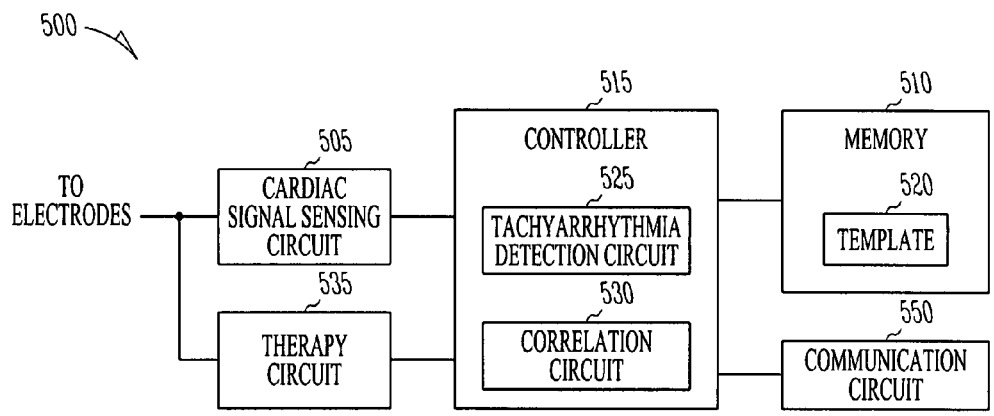
FIG. 5 is a block diagram of portions of an example of a device for providing cardiac arrhythmia therapy to a subject.

FIG. 5 is a block diagram of portions of an example of a device 500 for providing cardiac arrhythmia therapy to a subject. In this example, the device 500 includes an implantable cardiac signal sensing circuit 505, a memory 510, and a controller 515. The implantable cardiac signal sensing circuit 505 is configured for sensing an intrinsic cardiac signal. Intrinsic cardiac signals such as electrocardiogram (ECG) signals originate from electrophysiological signals originating in and propagated through the cardiac tissue, which provide for the cardiac muscle contraction that pumps blood through the body. Examples of cardiac signal sensing circuits include subcutaneous ECG circuits, intracardiac electrogram (EGM) sensing circuits, and wireless ECG circuits. A subcutaneous ECG sensing circuit generally includes electrodes that are implanted just beneath the skin, and the resulting ECG signal obtained is referred to as subcutaneous ECG or far-field electrogram. An intracardiac EGM circuit and a wireless ECG circuit generally include at least one electrode that is placed in or around the heart as described above. A wireless ECG generally includes a plurality of electrodes to provide differential sensing of cardiac signals to approximate a surface ECG.

The memory 510 stores at least one template 520 for calculating morphology correlations. In some examples, the template 520 includes a morphology of normal atrial-ventricular (A-V) conduction. In certain examples, the template 520 includes a morphology of a normal sinus rhythm (NSR). In certain examples, the template 520 includes a morphology of SVT.

The controller 515 may include a digital signal processor, application specific integrated circuit (ASIC), microprocessor, or other type of processor, interpreting or executing instructions in software or firmware. In some examples, the controller 515 may include a state machine or sequencer that is implemented in hardware circuits. The controller 515 may include any combination of hardware, firmware, or software. The controller 515 can include one or more circuits to perform the functions described herein. A circuit may include software, hardware, firmware or any combination thereof. For example, the circuit may include instructions in software executing on or interpreted by the controller 515. Multiple functions may be performed by one or more circuits.

In certain examples, the controller 515 includes a tachyarrhythmia detection circuit 525 and a correlation circuit 530. The tachyarrhythmia detection circuit 525 uses a sensed intrinsic cardiac signal to detect a rhythm that may indicate tachyarrhythmia. In some examples, the tachyarrhythmia detection circuit 525 detects ventricular tachyarrhythmia by detecting a rhythm with an elevated ventricular rate, for example. In some examples, the tachyarrhythmia detection circuit 525 detects ST when the detected elevation in rate is gradual rather than sudden (e.g., gradual rate onset rather than sudden rate onset).

In certain examples, the correlation circuit 530 is configured to iteratively calculate a correlation between the sensed intrinsic cardiac signal and the template 520. The calculated correlation can be compared to a variable correlation threshold such as to determine whether the detected rhythm with elevated ventricular rate correlates to the template 520. The device 500 can include a therapy circuit 535 configured to inhibit a therapy for treatment of VT when the detected rhythm correlates to the template according to a comparison of the calculated correlation to the variable correlation threshold.

An example of a calculated correlation is an FCC. The variable correlation threshold, to which the FCC is compared to determine correlation, is allowed to self-adjust or float. The variable correlation threshold may be referred to as a floating FCC threshold or $FFCC_{th}$. In some examples, the correlation circuit 530 can be configured for recurrently updating the $FFCC_{th}$ such as while the detected rhythm is present and the VT therapy is inhibited. The correlation circuit 530 can calculate $FFCC_{th}$ using a previous variable threshold value, such as together with a current calculated correlation. For example, $$FFCC_{th} = x(FFCC_{th}) + y(\text{current } FCC) \quad (1)$$

In certain examples, x and y are fractions. In an illustrative example, x and y are three-fourths (75%) and one-fourth (25%) respectively, for example.

The correlation circuit 530 can initialize the value of the $FFCC_{th}$. In some examples, the correlation circuit 530 initializes the $FFCC_{th}$, with the value of the fixed $FCC_{th}$. In some examples, the correlation circuit 530 initializes the $FFCC_{th}$ by using a central tendency (e.g., an average, median, mode, or the like) of a number (e.g., 4) of calculated FCCs that exceed a threshold FCC value. Outlying FCCs can be discarded from the central tendency determination. In some examples, the correlation circuit 530 initializes the $FFCC_{th}$ by averaging a number of calculated FCCs that exceed a percentage or fraction of the fixed $FCC_{th}$ (e.g., 0.95 (fixed $FCC_{th}$)).

The device 500 can include a communication circuit 550 coupled to the controller 515 and configured to communicate information with an external device. The correlation circuit 530 can be configured to receive the fixed correlation threshold from the external device.

The device 500 can include a therapy circuit 535 that can be communicatively coupled to the controller 515. The therapy circuit 535 can be configured to inhibit the VT therapy while the detected rhythm is deemed ST and when the detected rhythm correlates to the template, such as according to the comparison of the calculated correlation (e.g., FCC) to the variable correlation threshold (e.g., $FFCC_{th}$).

In some examples, it may be desirable to begin calculating the variable correlation threshold before the tachyarrhythmia detection circuit 525 deems that the ventricular rate is elevated to a point to begin calculating the correlations. For example, the correlation circuit 530 can be configured to begin updating the variable correlation threshold when the tachyarrhythmia detection circuit 525 detects a rhythm with an elevated ventricular rate that is within a specified rate below a lowest VT rate zone (e.g., twenty beats per minute, or 20 bpm, below the lowest VT rate zone). This approach may allow more detected beats to correlate because the variable correlation threshold is allowed to self-adjust earlier.

Figure 6:
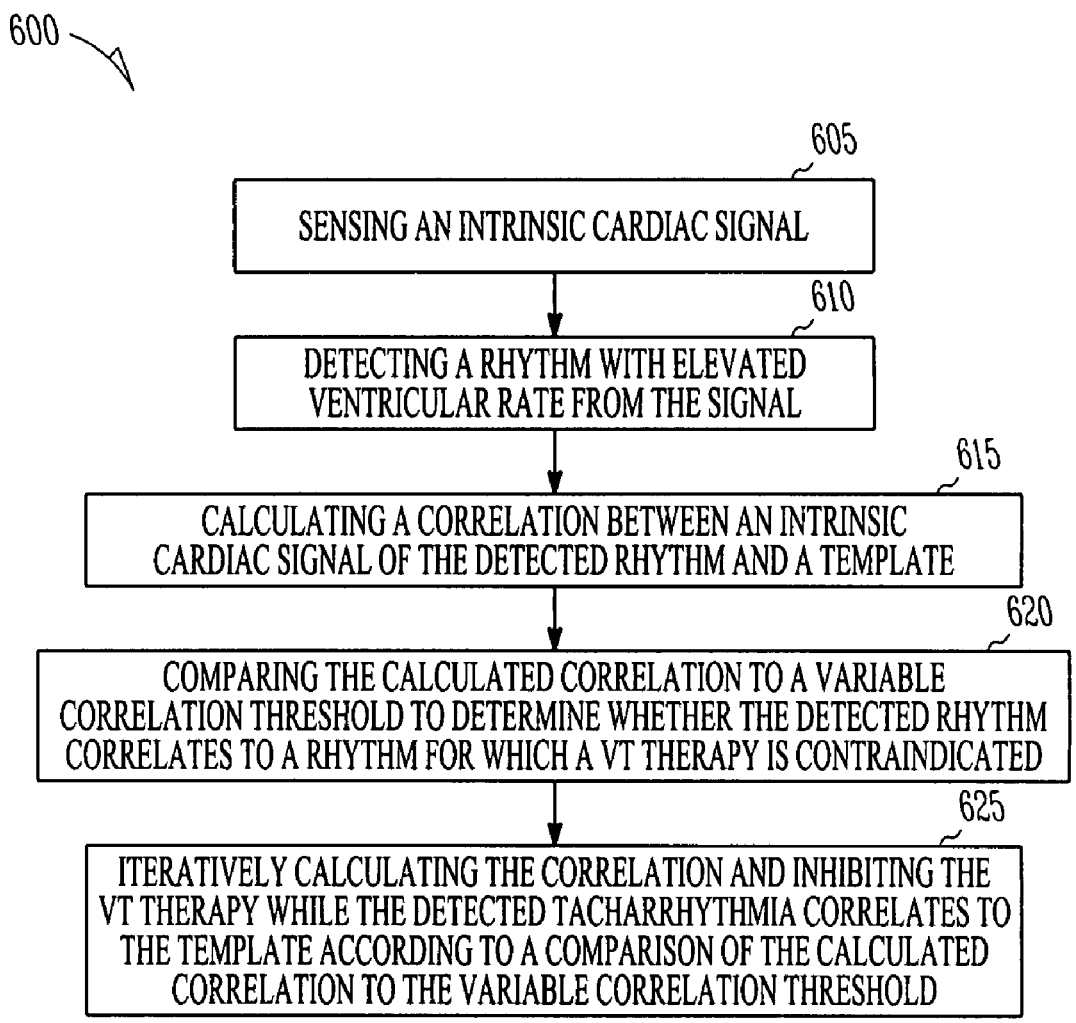
FIG. 6 is a flow diagram of a method for providing cardiac arrhythmia therapy to a subject.

FIG. 6 is a diagram of a method 600 for providing cardiac arrhythmia therapy to a subject. At 605, an intrinsic cardiac signal is sensed. At 610, rhythm with elevated ventricular rate is detected from the cardiac signal. At 615, a correlation is calculated between at least one intrinsic cardiac signal of the detected rhythm and a template. In some examples, the template includes a morphology of normal atrial-ventricular (A-V) conduction. At 620, the calculated correlation is compared to a variable correlation threshold to determine whether the detected rhythm correlates to a rhythm for which a VT therapy is contraindicated. At 625, the correlation is iteratively calculated and the VT therapy is inhibited while the detected rhythm correlates to the template, such as according to a comparison of the calculated correlation to the variable correlation threshold.

In FIG. 5, in some examples, the correlation circuit 530 is configured to determine whether the calculated correlation (e.g., FCC) exceeds a fixed correlation threshold (e.g., fixed $FCC_{th}$) before the comparison to the variable threshold is made. For example, if the detected rhythm correlates to the template 520 (e.g., for ST) using the fixed threshold, and the variable threshold is lower than the fixed threshold, then the comparison to the fixed correlation threshold is replaced on later beats with the comparison to the variable correlation threshold. As an illustrative example, the fixed $FCC_{th}$ may be set to 0.94. If $FCC \geq 0.94$ and $FFCC_{th} < 0.94$, then a comparison to the $FFCC_{th}$ is used, instead of a comparison to the fixed $FCC_{th}$ of 0.94, to establish correlation to the template 520. Correlation continues to be established using $FFCC_{th}$ while the detected rhythm is deemed ST, when the detected rhythm is correlated to the template 520 using the fixed threshold, and when the variable correlation threshold is lower than the fixed correlation threshold (e.g., $FCC_{th}=\min(\text{fixed } FCC_{th}@0.94, FFCC_{th})$).

In some examples, the correlation circuit 530 can use a scaling factor sf to further modify the variable correlation threshold, such as to provide more flexibility to the calculation to cause more correlated beats to occur (e.g., $FCC_{th}=\min(\text{fixed } FCC_{th}@0.94, sf*FFCC_{th})$). As an illustrative example, the sf is 0.99 and $FCC_{th}=\min(\text{fixed } FCC_{th}@0.94, (0.99)(FFCC_{th}))$. Because the scaling factor reduces the variable correlation threshold, more detected beats or rhythms will correlate. In some examples, the correlation circuit can impose a lowest or minimum value for restricting the variable correlation threshold. This prevents the variable correlation threshold from going too low and allowing too much correlation. Examples of a minimum correlation threshold value include 0.6 and 0.8. For example, if the minimum threshold value was 0.6, then $FCC_{th}=\max(\min(\text{fixed } FCC_{th}@0.94, FFCC_{th}), 0.6)$.

In some examples, the variable correlation threshold can be recurrently updated, such as when there are no sudden changes in the correlation calculation. In some examples, it is declared that there are no sudden changes in the correlation calculation when the calculated correlation stays within a range of the variable correlation threshold. For example, the correlation circuit 530 may recurrently update $FFCC_{th}$ according to equation (1) when $FCC > (0.95)(FFCC_{th})$.

Figure 7A:
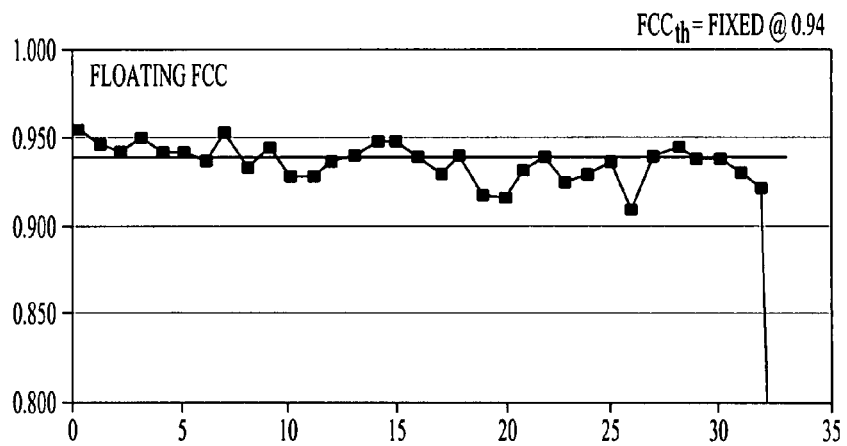
FIGS. 7A-7C show examples of correlation thresholds.
Figure 7B:
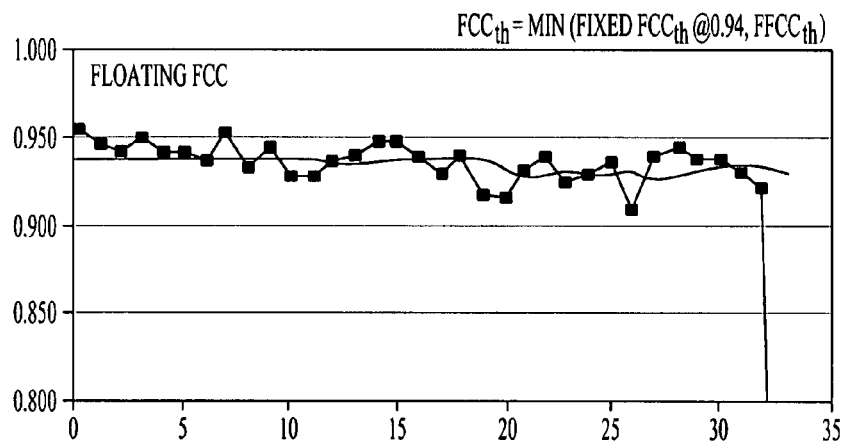
Figure 7C:
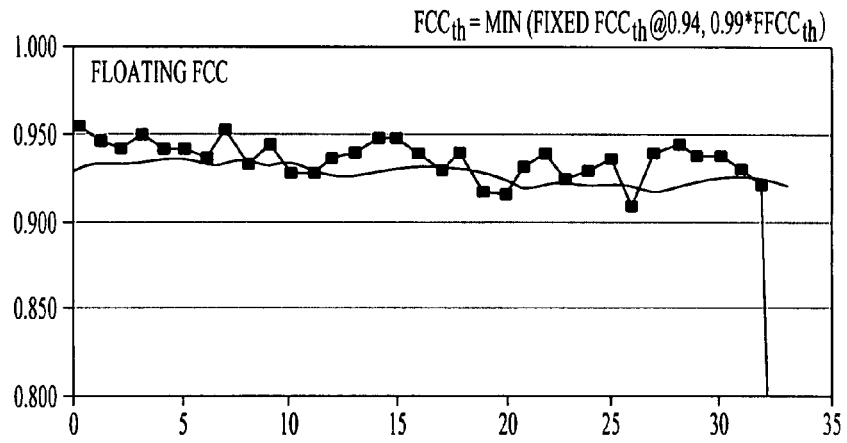

FIGS. 7A-7C show examples of correlation thresholds. FIG. 7A shows a fixed correlation threshold (fixed $FCC_{th}$) set to 0.94 and calculated correlation coefficients. In this example, correlation coefficients were calculated for 32 heart beats. FIG. 7B shows a variable correlation threshold ($FFCC_{th}$). FIG. 7C shows a variable correlation threshold ($FFCC_{th}$) modified with a scaling factor. The examples show that allowing the correlation threshold to float will generally result in more correlated beats, such as when the rhythm is ST and the calculated correlations are gradually decreasing, for example.

In some examples, the cardiac signal sensing circuit 505 in FIG. 5 includes at least one implantable electrode shaped or sized or otherwise configured to sense an intrinsic cardiac signal in an atrium and at least one implantable electrode shaped or sized or otherwise configured to sense an intrinsic cardiac signal in a ventricle. If a detected rhythm is ST, a sudden increase in the rate should not occur. In some examples, the tachyarrhythmia detection circuit 525 can be configured to determine that the detected rhythm with elevated ventricular rate is not ST if there are one or more sudden increases in the rate.

Examples of a sudden change that may indicate that the rhythm is not ST include: i) a measured increase in heart rate exceeding a specified heart rate threshold within a specified time period, ii) a P-wave to R-wave (P-R) interval of the detected rhythm decreases from a baseline P-R interval value by at least a specified threshold value within a specified time period, and iii) an increase in a ventricular contraction (V) rate that exceeds an atrial contraction (A) rate within a specified time period. In certain examples, detecting a sudden increase in V rate that exceeds the A rate includes detecting that the V rate exceeds the A rate by a specified amount within the specified time period. In certain examples, detecting a sudden increase in V rate that exceeds the A rate includes detecting a sudden change in a ratio including V rate and A rate. For instance, detecting a sudden increase in V rate that exceeds the A rate may include determining that a ratio of the A rate to the V rate (A/V) decreases from a baseline ratio value by a specified threshold within the specified time period.

Figure 8:
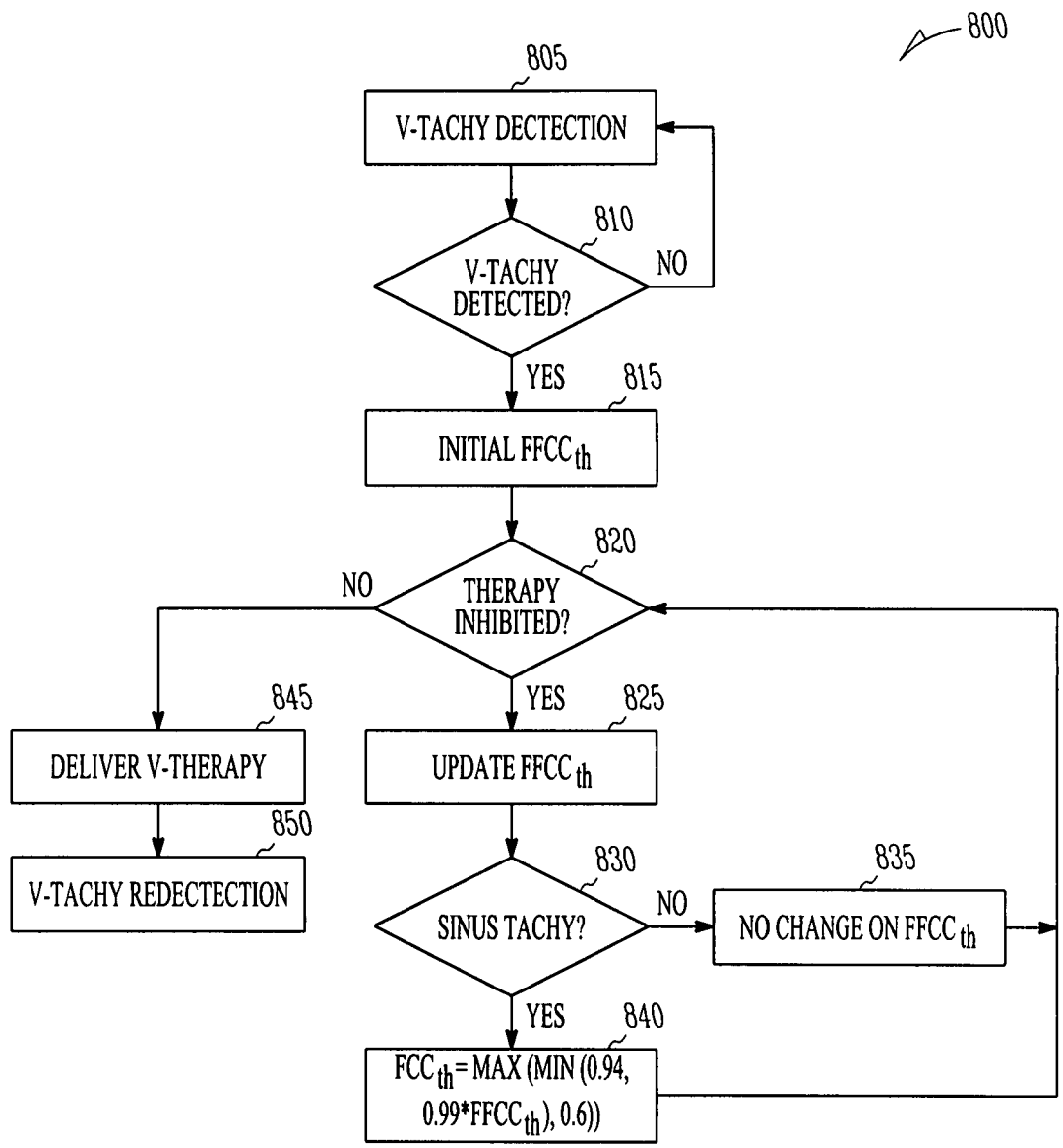
FIG. 8 is a flow diagram of a method for providing cardiac arrhythmia therapy using a variable correlation threshold.

FIG. 8 is a diagram of a method 800 for providing cardiac arrhythmia therapy using a variable correlation threshold. At 805 and 810 it is determined whether ventricular tachyarrhythmia is detected, such as by an elevated ventricular rate for example. If the rate becomes elevated gradually (gradual onset), the ventricular tachyarrhythmia may be ST. An initial variable correlation rate threshold is determined at 815. While therapy for the ventricular tachyarrhythmia is inhibited at 820, the variable correlation rate threshold is updated at 825. If the rhythm is not determined to be ST at 830, the correlation threshold is not changed at 835. If the rhythm is determined to be ST at 830 then the correlation threshold is changed at 840 (e.g., $FCC_{th}$=max(min(fixed $FCC_{th}$@0.94, $FFCC_{th}$), 0.6)). If the therapy is not inhibited, (e.g., because initially the rhythm does not correlate using the fixed threshold and then does not correlate using the variable threshold) then therapy is delivered at 845. After therapy, one or more redetection schemes can be initiated at 850, such as to determine whether the arrhythmia persists or reoccurs even after therapy is provided.

Figure 9:
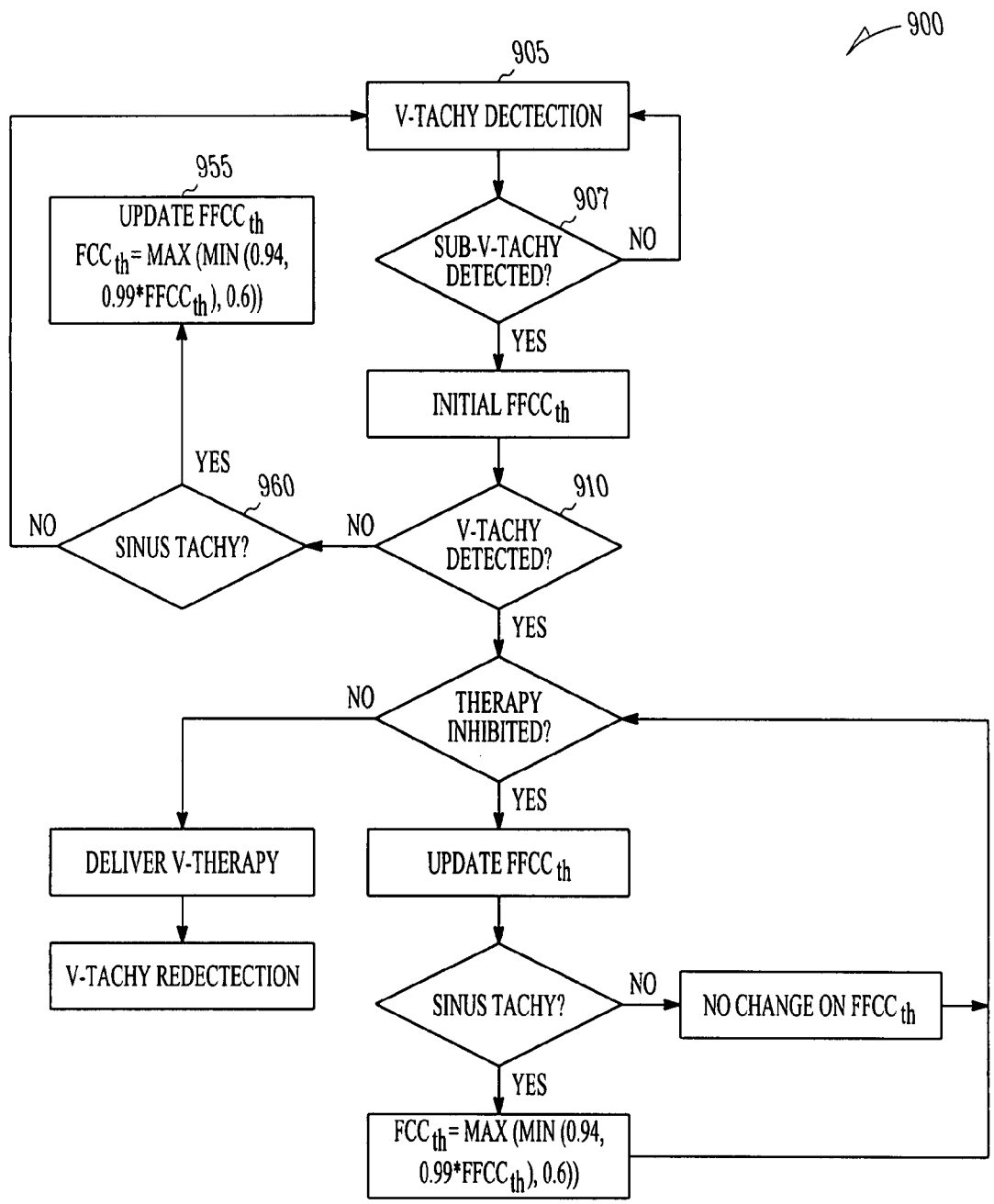
FIG. 9 is a flow diagram of another method for providing cardiac arrhythmia therapy using a variable correlation threshold.

FIG. 9 is a diagram of another method 900 for providing cardiac arrhythmia therapy using a variable correlation threshold. In this method 900, calculating the variable correlation threshold begins before it is determined that the ventricular rate is elevated into the lowest tachyarrhythmia rate zone. The method 900 is similar in some respects to the method of FIG. 8, but FIG. 9 includes an extra loop to begin calculating the variable correlation coefficient. At 905 and 907 it is determined whether ventricular tachyarrhythmia is detected, such as by an elevated rate that is within a specified rate (e.g., 20 b.p.m.) below the lowest tachyarrhythmia rate zone used for declaring a tachyarrhythmia based upon rate. At 910 it is determined whether ventricular tachyarrhythmia is detected, such as by the ventricular rate elevating into one of the tachyarrhythmia rates zones, for example. If not, then updating of the variable correlation threshold can be begun while the rhythm is determined to be ST at 955 and 960.

When using a fixed correlation threshold, sometimes heart rhythms such as atrial fibrillation (AF) or atrial flutter (AFL) that are marginally uncorrelated will be treated. Providing a variable correlation threshold may allow less deliveries of shock therapy by resulting in more rhythms being correlated. In some examples, the tachyarrhythmia detection circuit 525 in FIG. 5 is configured for declaring the rhythm with elevated ventricular rate as atrial tachyarrhythmia. In certain examples, tachyarrhythmia detection circuit 525 deems the rhythm with elevated ventricular rate as atrial tachyarrhythmia if the atrial contraction rate exceeds an atrial tachyarrhythmia rate threshold and the ventricular rhythm is unstable. In some examples, the stability can be assessed by determining whether the ventricular rhythm is unstable using a measure of variability of the ventricular time intervals. In some examples, the stability can be assessed from variability of the intervals in combination with a measurement of another physiologic parameter. In certain examples, tachyarrhythmia detection circuit 525 declares the rhythm with elevated ventricular rate as an atrial tachyarrhythmia if there is a sudden change in a ratio of an atrial contraction (A) rate to a ventricular contraction (V) rate (e.g., the ratio changes from a baseline A rate to V rate ratio by at least a specified threshold value within a specified period of time).

The correlation circuit 530 can be configured to compare a calculated correlation to a fixed correlation threshold, such as before the comparison to the variable correlation threshold, to determine whether the detected rhythm is correlated to the template. In certain examples, the correlation circuit 530 replaces the comparison to the fixed correlation threshold with the comparison to the variable correlation threshold while the detected rhythm is deemed an atrial tachyarrhythmia and when the detected rhythm is correlated to the template and the variable correlation threshold is lower than the fixed threshold. The therapy circuit 535 can be configured to inhibit the VT therapy while the detected rhythm is deemed an atrial tachyarrhythmia, and when the detected rhythm correlates to the template, such as according to the comparison of the calculated correlation to the variable correlation threshold.

Figure 10:
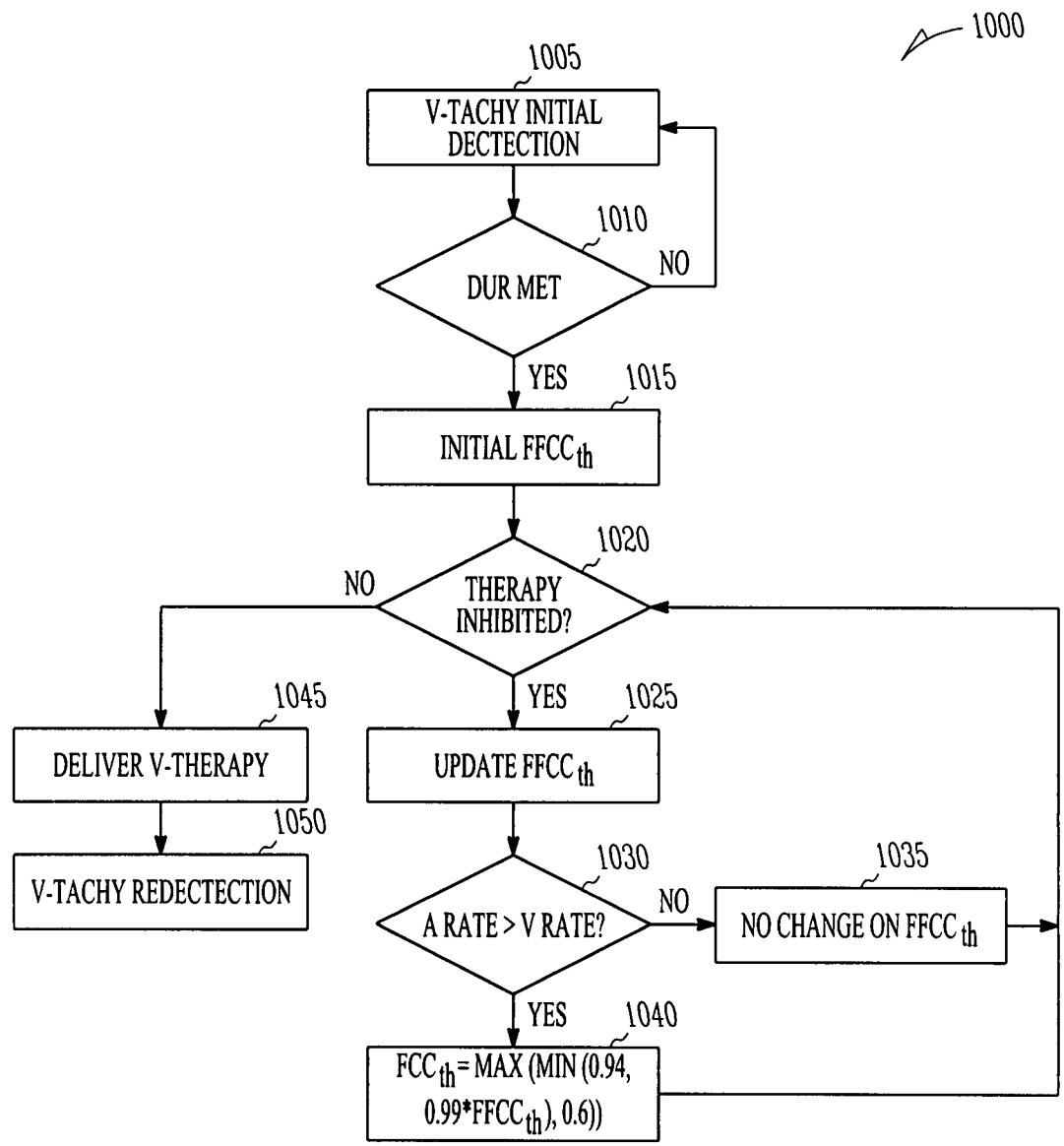
FIG. 10 is a flow diagram of another method for providing cardiac arrhythmia therapy using a variable correlation threshold.

FIG. 10 is a diagram of another method 1000 for providing cardiac arrhythmia therapy using a variable correlation threshold. At 1005 and 1010 it is determined whether ventricular tachyarrhythmia is detected, such as by an elevated ventricular rate for example and the duration of the rhythm for example. An initial variable correlation threshold is determined at 1015. While therapy for the ventricular tachyarrhythmia is inhibited at 1020, the variable correlation rate threshold is updated at 1025. If the atrial rate does not exceed the ventricular rate then the rhythm is not determined to be AF or AFL at 1030 and the correlation threshold is not changed at 1035. If the atrial rate does exceed the ventricular rate then the rhythm is determined to be AF or AFL at 1030 and the correlation threshold is changed at 1040 (e.g., $FCC_{th}$=max(min (fixed $FCC_{th}$@0.94, $FFCC_{th}$), 0.6)). If the therapy is not inhibited, (e.g., because initially the rhythm does correlate using the fixed threshold and then using the variable threshold) then therapy is delivered at 1045. After therapy, one or more redetection schemes may be initiated at 1050.

Figure 11:
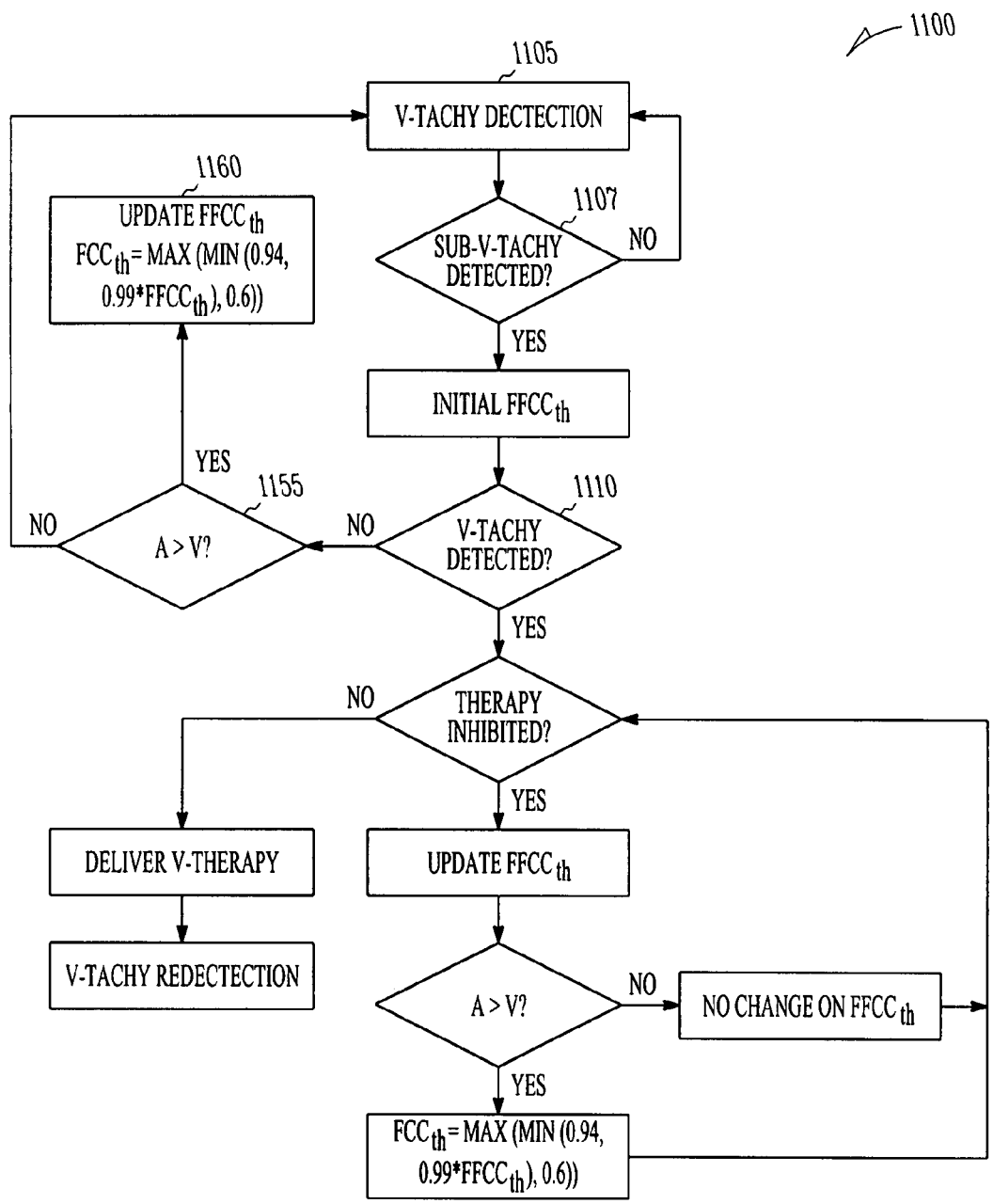
FIG. 11 is a flow diagram of another method for providing cardiac arrhythmia therapy using a variable correlation threshold.

FIG. 11 is a diagram of another method 1100 for providing cardiac arrhythmia therapy using a variable correlation threshold. In this method 1100, calculating the variable correlation threshold begins before it is determined that the ventricular rate is elevated into the lowest tachyarrhythmia rate zone. The method 1100 is similar to method of FIG. 10 in some respects, but FIG. 11 includes an extra loop to begin calculating the variable correlation coefficient. At 1105 and 1107 it is determined whether ventricular tachyarrhythmia is detected by an elevated rate that is within a specified rate (e.g., 20 bpm) below the lowest tachyarrhythmia rate zone. At 1110, it is determined whether ventricular tachyarrhythmia is detected, such as by the ventricular rate elevating into one of the tachyarrhythmia rates zones, for example. If not, then updating of the variable correlation threshold can be begun while the rhythm is determined to be AF or AFL at 1155 and 1160.

The methods described herein can be combined. For example, the method of FIGS. 8 and 10 can be combined into a method to detect both ST and AF/AFL by including the check for ST at 830 into the method of FIG. 10 after or before the check for AF/AFL at 1030.

As described previously, a morphology-based rhythm detection, identification, or classification method typically compares features of the morphological shape of a cardiac depolarization to a template morphology, such as to classify tachyarrhythmia, for example. In certain examples, a fiducial point in the rhythm template and a fiducial position in the detected rhythm are automatically temporally aligned, and then a correlation value is calculated, such as according to the similarity of the rhythm to the template. The temporal shifting of the sensed morphology (e.g., due to sampling granularity or otherwise) relative to the fiducial point can cause low correlation and may lead to delivery of unnecessary shock therapy.

Figure 12:
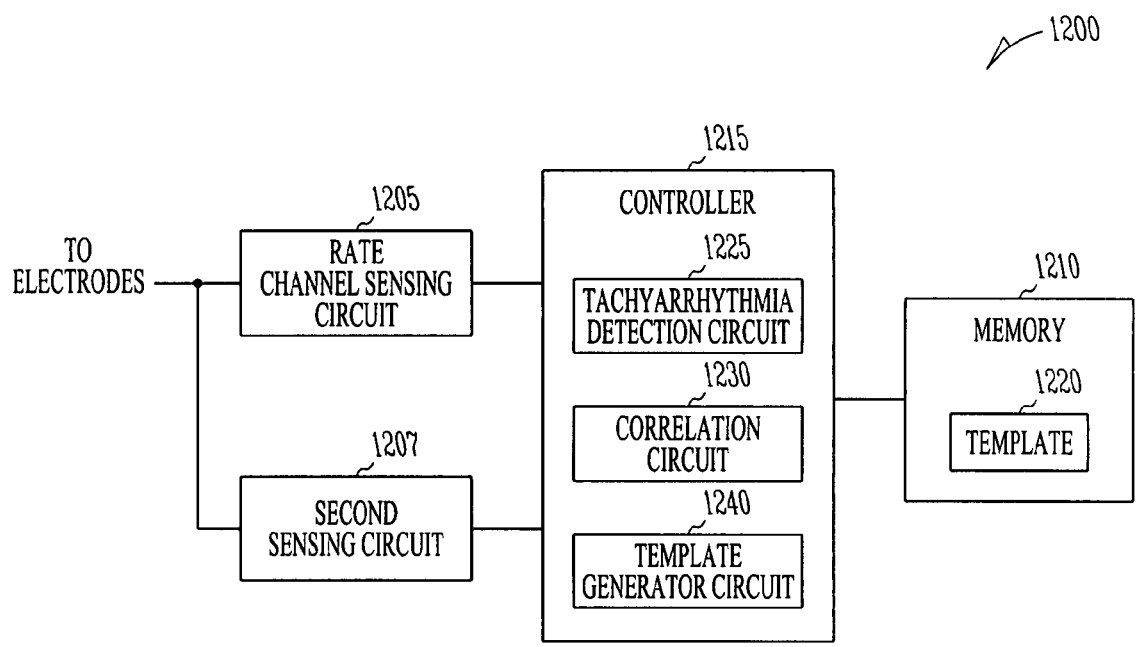
FIG. 12 is a block diagram of portions of an example of a device to identify tachyarrhythmia.

FIG. 12 is a block diagram of portions of an example of a device 1200 to identify tachyarrhythmia. In this example, the device 1200 includes a rate channel sensing circuit 1205, a second sensing circuit 1207, a memory 1210, and a controller 1215. In certain examples, the rate channel sensing circuit 1205 includes or is coupled to at least one implantable heart rate sensing electrode. For example, the rate channel sensing circuit 1205 may include or be coupled to the tip electrode 120A and either the ring electrode 120B or defibrillation electrode 118 in FIG. 1. In certain examples, the second sensing circuit 1207 includes or is coupled to at least one second sensing electrode. For example, the second sensing circuit 1207 may be a shock channel and the second sensing electrode may include defibrillation electrode 118, defibrillation electrode 116, or an electrode on the device housing, header, or can 105.

The memory 1210 can store at least one template 1220 and the controller 1215 can include a tachyarrhythmia detection circuit 1225, a correlation circuit 1230, and a template generator circuit 1240. The tachyarrhythmia detection circuit 1225 can use a sensed intrinsic cardiac signal to detect a rhythm, such as for generating a template. The rhythm may include a normal sinus rhythm (NSR).

Figure 13:
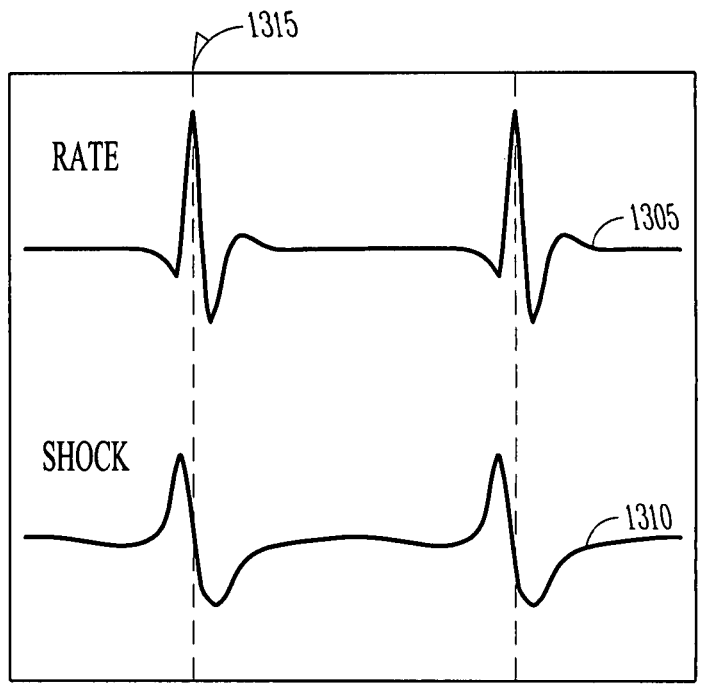
FIG. 13 shows an illustration of cardiac signals for generating a template.

The template generator circuit 1240 can be configured for generating the template 1220 using a first signal sensed using the rate channel sensing circuit 1205 during an NSR, and a second signal sensed using the second sensing circuit 1207 during the NSR. The template 1220 generated includes a fiducial point on the first sensed signal and correlation features on the second sensed signal. FIG. 13 illustrates cardiac signals sensed during NSR for generating the template 1220. The first sensed signal 1305 is sensed using the rate channel sensing circuit 1205 and includes fiducial point 1315. The fiducial "point" (or location) may include one or more samples of a sampled signal or a range of samples. Typically, the fiducial point can be the positive peak point or the negative peak point of the rate channel. The second sensed signal 1310 can be sensed at the same time using the second sensing circuit 1207. In this example, the second sensing circuit 1207 includes a shock channel.

Figure 14:
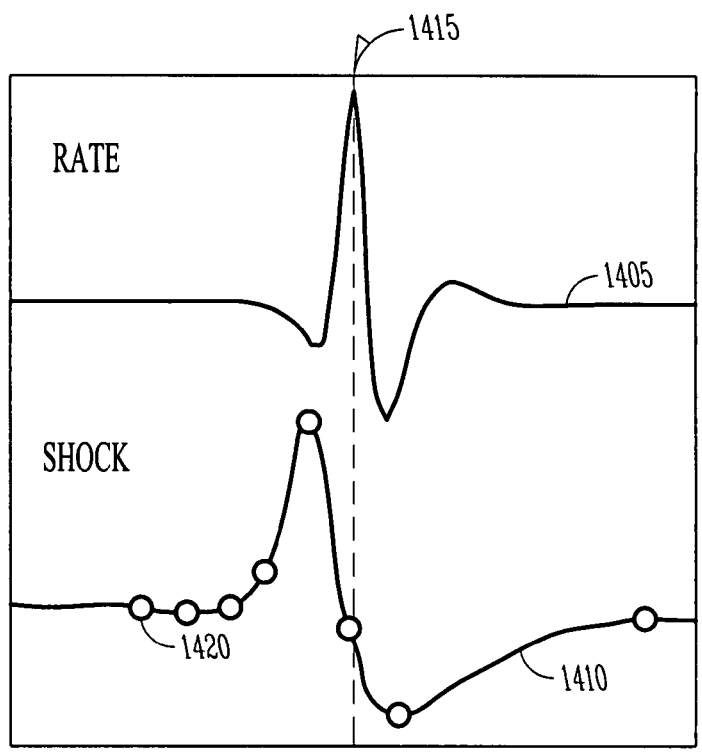
FIG. 14 shows an illustration of cardiac signals for generating the template.

FIG. 14 also illustrates sensed cardiac signals for generating the template. In this example, the fiducial point 1415 can be chosen from the QRS complex of the first sensed signal 1405. A number of correlation features 1420 on the shock channel can be selected. In the example shown, eight features are selected. To generate the template 1220, the correlation feature 1420 amplitudes and times relative to the fiducial point 1415 can be determined and stored in memory 1210 and used for rhythm classification. Sensed signals that have abnormal conduction rhythms such as (VT) can have different signal characteristics than the signals for NSR or signals sensed for SVT.

Figure 15:
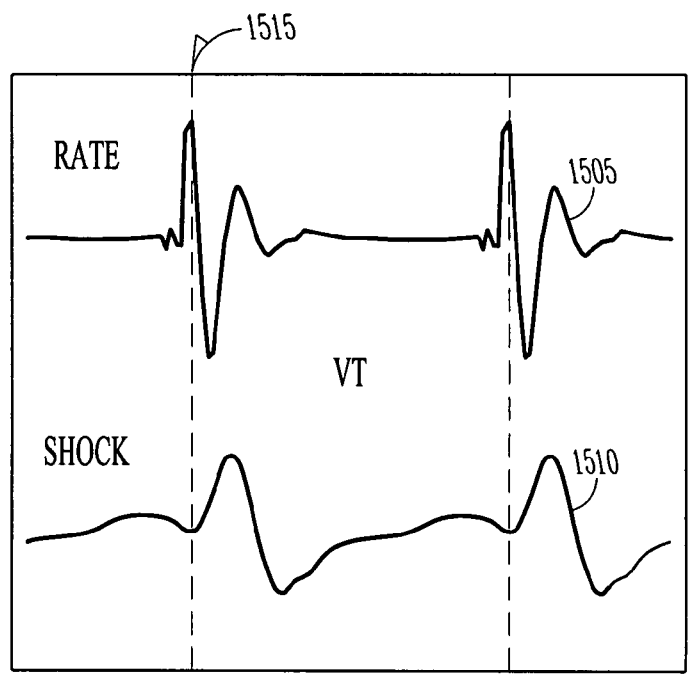
FIG. 15 shows an illustration of cardiac signals sensed during VT.

FIG. 15 illustrates two additional intrinsic cardiac signals that are sensed during VT. In this example, the third sensed cardiac signal 1505 can be sensed using the rate channel sensing circuit 1205. The fourth sensed cardiac signal 1510 can be sensed at the same time as the third sensed signal 1505 using the second sensing circuit 1207 that includes a shock channel. The signals corresponding to VT have different relative timing and other signal characteristics than the signals for NSR in FIG. 13. A first fiducial position is chosen on the third signal 1505. In the illustrations, the first fiducial position corresponds to the QRS complex.

Figure 16:
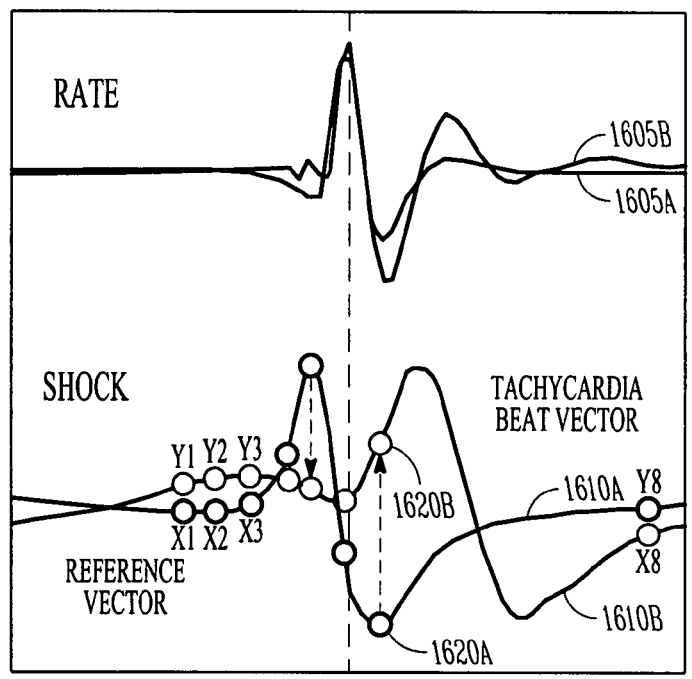
FIG. 16 shows an illustration of cardiac signals aligned for calculating a correlation coefficient.

FIG. 16 illustrates the four signals aligned for calculating the correlation coefficient (e.g., FCC). The illustration shows the four signals 1605A, 1605B, 1610A, 1610B aligned using the first fiducial position. Correlation features 1620B in the fourth signal are identified from alignment in time with correlation features 1620A in the template 1220. To calculate a correlation coefficient, the correlation circuit 1230 identifies the first fiducial position in a third signal and aligns the correlation features 1620A of the template 1220 (from the second signal 1610A) and the correlation features 1620B of the fourth sensed signal 1610B. Each correlation feature includes an amplitude and a time from the alignment point.

Eight correlation features (x1 ... x8) are shown for the fourth signal 1610B and eight correlation features (y1 ... y8) are shown for the second signal 1610A or the template signal. In some examples, a correlation coefficient is calculated as $$FCC = \frac{\left(8\sum_{i=1}^{8} x_i y_i - \left(\sum_{i=1}^{8} x_i\right)\left(\sum_{i=1}^{8} y_i\right)\right)^2}{\left(8\sum_{i=1}^{8} x_i^2 - \left(\sum_{i=1}^{8} x_i\right)^2\right)\left(8\sum_{i=1}^{8} y_i^2 - \left(\sum_{i=1}^{8} y_i\right)^2\right)}. \quad (2)$$

Figure 17:
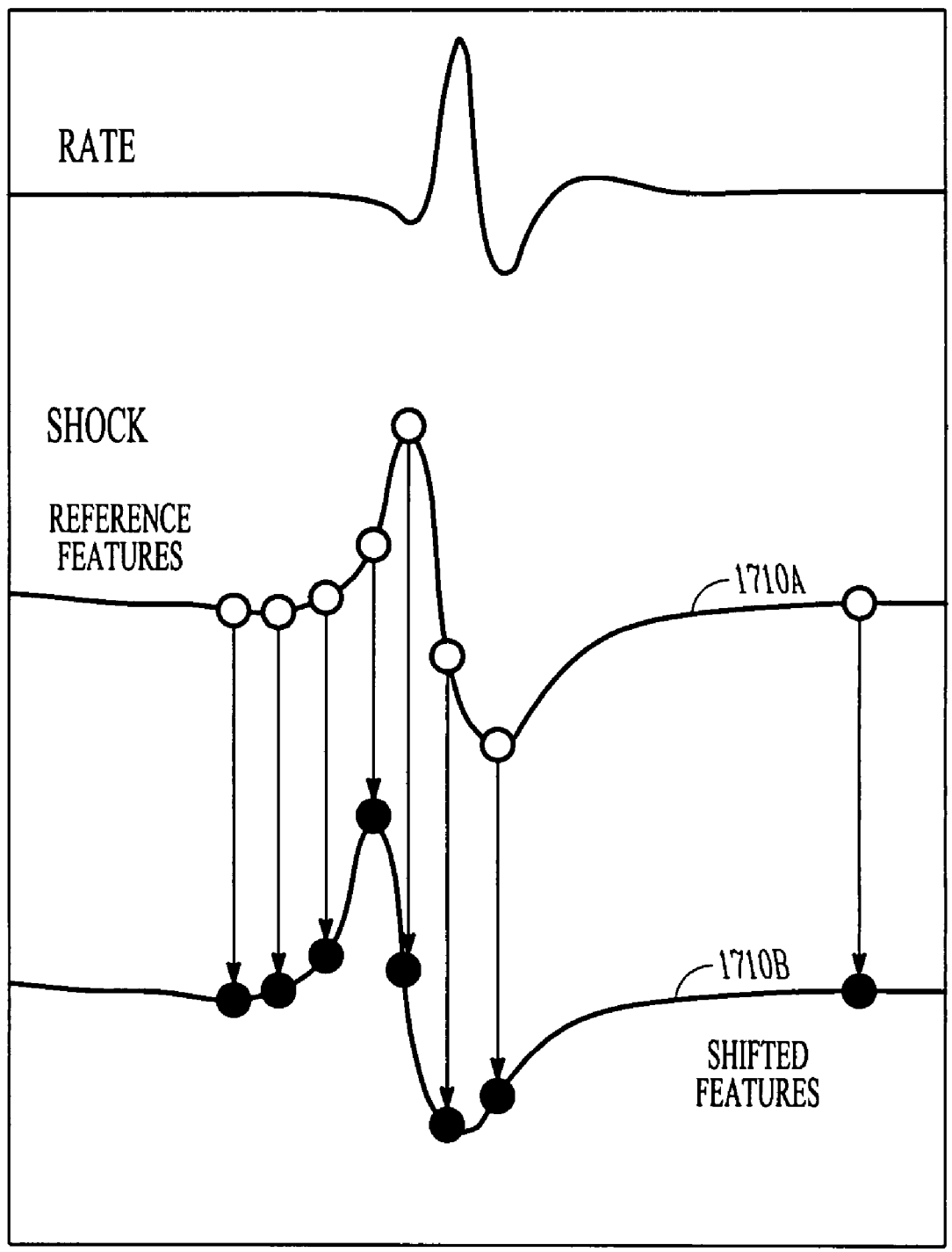
FIG. 17 shows another illustration of cardiac signals aligned for calculating the correlation coefficient.

As heart rate accelerates, during SVT, ST, AF, or AFL the signal sensed using the second sensing circuit 1207 may shift with respect to the signal sensed using the rate channel sensing circuit 1205. Shifting of the relative timing of the shock channel signal (or fourth signal) with respect to the fiducial point of the rate channel signal (or third signal) can cause lower correlation. FIG. 17 illustrates an unshifted shock channel signal 1710A and a shifted shock channel signal 1710B for the same fiducial point of the rate channel signal. The correlation coefficient will be lower even though the signal correlates well visually.

In some examples, the correlation circuit 1230 is configured for choosing a second fiducial position in the third signal that is shifted from the first fiducial position by at least one sample. The correlation circuit 1230 re-aligns the correlation features of the fourth signal using the second fiducial position. For example, to shift the sensed signal 1710B to the right (later in time), one sample time is added to each correlation point. The correlation circuit then re-calculates the correlation using the template correlation features and the shifted correlation features of the fourth signal. The correlation circuit 1230 then determines whether the detected rhythm with elevated ventricular rate correlates to the contraindicated rhythm using a maximum calculated correlation coefficient.

In some examples, if the largest correlation coefficient consistently comes from a shifted signal, then the alignment of the shifted signal should be adopted. In some examples, the correlation circuit 1230 is configured for replacing the first fiducial position of the third signal (1605B in FIG. 16) with the second fiducial position when the re-aligning using the correlation features of the second fiducial position yields the maximum calculated correlation during a plurality of correlations calculated during the detected rhythm.

The cardiac signal sensed using the second sensing circuit 1207 may shift either earlier or later with respect to the signal sensed using the rate channel sensing circuit 1205. In some examples, the correlation circuit 1230 chooses a second fiducial position in the third signal that is earlier than the first fiducial position by at least one sample. For example, the second fiducial position can be chosen by shifting the first fiducial position one sample to the left (earlier). The correlation circuit 1230 re-aligns the correlation features of the fourth signal using the second fiducial position and calculates a second correlation using the template correlation features and the correlation features of the fourth signal.

The correlation circuit 1230 then chooses a third fiducial position in the third signal that is later than the first fiducial position by at least one sample. The correlation circuit 1230 re-aligns the correlation features of the fourth signal using the second fiducial position and calculates a third correlation using the template correlation features and the correlation features of the fourth signal.

The correlation circuit 1230 then determines whether the detected rhythm with elevated ventricular rate correlates to the contraindicated rhythm using a maximum calculated correlation coefficient. In some examples, the correlation circuit 1230 replaces the first fiducial position of the third signal with either second fiducial position or the third fiducial position according to which fiducial position yields the maximum calculated correlation during a plurality of correlations calculated during the detected rhythm.

In some examples, the correlation circuit 1230 searches for a new fiducial position in the third cardiac signal. The correlation circuit 1230 may begin such a search if the calculated correlation coefficients have become lower, or the correlation circuit 1230 may be configured to iteratively search for a new fiducial point. In certain examples, the search is begun according to a number of sensed heart beats, such as searching every N beats or cardiac cycles, where N is an integer (e.g., N=4).

Figure 18:
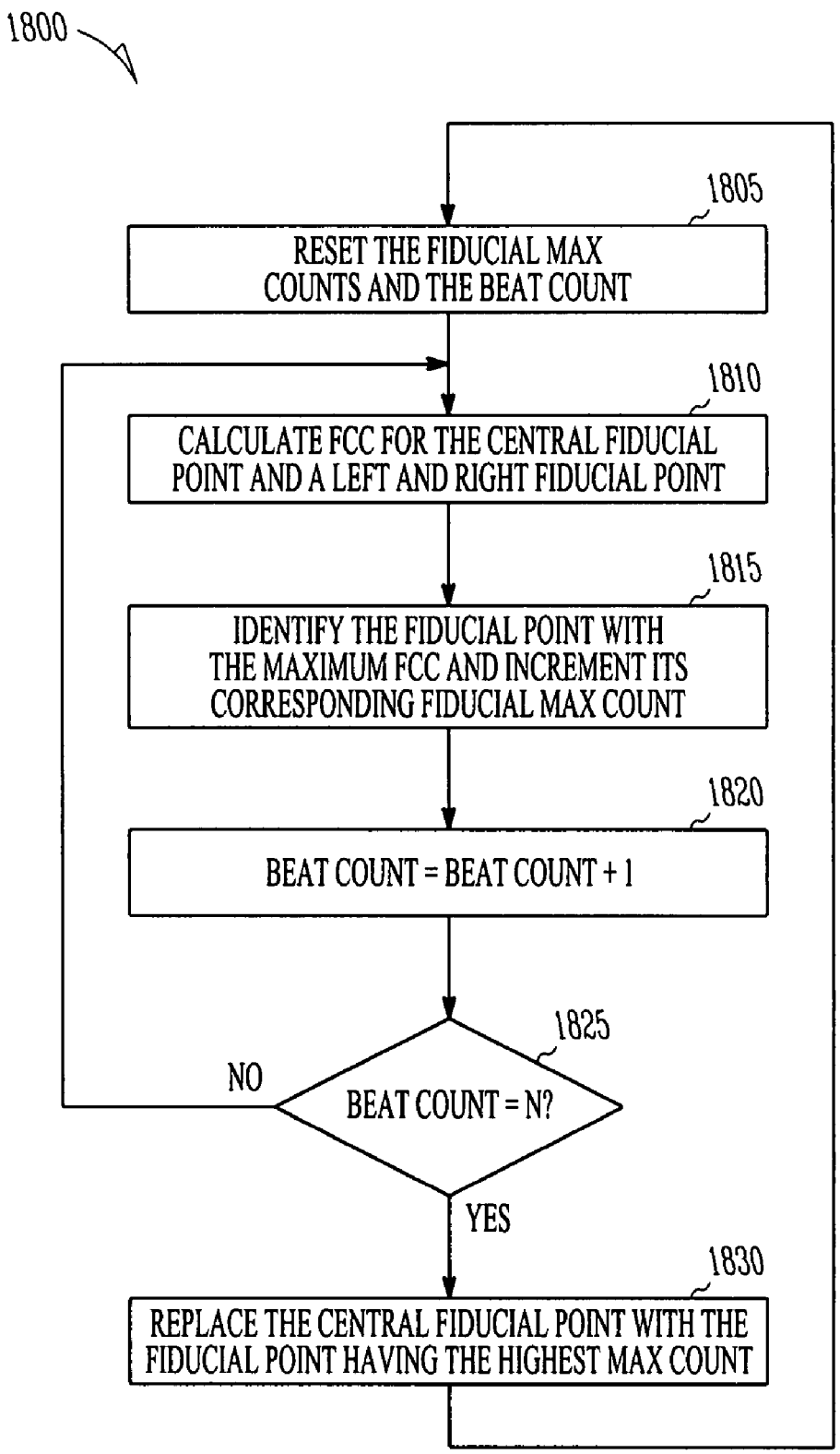
FIG. 18 shows a diagram of an example of a method of searching for a new fiducial point or a new fiducial position.

FIG. 18 shows a diagram of an example of a method 1800 of searching for a new fiducial point or a new fiducial position. In this example, a central fiducial point is identified as are a fiducial point left (earlier) of the central fiducial point and a fiducial point right (later) of the central fiducial point. As an example, the central fiducial point corresponds to the first fiducial position of the third cardiac signal and the left fiducial point is one sample position earlier than the first fiducial position and the right fiducial point is one sample position later than first fiducial position. The left and right fiducial points can be shifted by more than one sample from the central fiducial point.

Each of the fiducial positions can be assigned a fiducial max count. This count can be incremented when a calculated correlation for a cardiac cycle or heart beat is a maximum for the fiducial point. At 1805, the fiducial max counts and the heart beat count can be reset. At 1810, a correlation (e.g., FCC) is calculated for the central, left, and right fiducial points. At 1815, the fiducial point having the maximum correlation can be identified and its max count can be incremented. At 1820 the beat count can be incremented. At 1825, the if the beat count is less than N, the correlation for the next beat can be calculated. If the beat count is equal to N, the fiducial point having the greatest number of max counts during the last N beats replaces the central fiducial point. The counts are reset at 1805. The central fiducial point can be updated, if necessary, every N heart beats. Thus, lower correlations due to shifting of the relative timing of the shock channel signal with respect to the fiducial point of the rate channel signal can be reduced or minimized by searching for a better or best central fiducial point for alignment.

In some examples, a new central fiducial point is not allowed to be shifted from the original central fiducial point by more than a specified time interval (e.g., 15 ms). Such limiting of the search for a new central fiducial point may prevent correlating to VT beats.

Final Notes:

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   an implantable cardiac signal sensing circuit configured to provide an electrical cardiac signal representative of sensed cardiac activity of a subject;
   a memory to store at least one template, wherein the template includes a morphology of normal atrial-ventricular (A-V) conduction;
   a controller, communicatively coupled to the cardiac signal sensing circuit and the memory, including:
      a tachyarrhythmia detection circuit configured to detect a rhythm with elevated ventricular rate using the electrical cardiac signal;
      a correlation circuit configured to:
         iteratively calculate a value of correlation between the electrical cardiac signal and the template; and
         compare the calculated correlation value to a device-variable correlation threshold to determine whether the detected rhythm with elevated ventricular rate correlates to the template; and
      a therapy circuit configured to inhibit ventricular tachycardia (VT) therapy when the detected rhythm correlates to the template according to a comparison of the calculated correlation value to the device-variable correlation threshold.

2. The apparatus of claim 1, wherein the correlation circuit is configured to recurrently update the device-variable correlation threshold while the detected rhythm with elevated ventricular rate is present and the VT therapy is inhibited, wherein the updating uses a previous variable threshold value and a current calculated correlation.

3. The apparatus of claim 1, wherein the correlation circuit is configured to begin updating the device-variable correlation threshold when the rhythm with elevated ventricular rate is within a specified rate below a lowest VT rate zone.

4. The apparatus of claim 1, wherein the correlation circuit is configured to:
   compare the calculated correlation value to a fixed correlation threshold before the comparison to the device-variable correlation threshold;
   replace the comparison to the fixed correlation threshold with the comparison to the device-variable correlation threshold while the detected rhythm with elevated ventricular rate is deemed a sinus tachycardia (ST), when the detected rhythm is initially correlated to the template using the fixed correlation threshold, and when the device-variable correlation threshold is lower than the fixed correlation threshold; and
   wherein the therapy circuit is configured to inhibit VT therapy while the detected rhythm with elevated ventricular rate is deemed ST and when the detected rhythm with elevated ventricular rate correlates to the template according to the comparison of the calculated correlation value to the device-variable correlation threshold.

5. The apparatus of claim 4, including:
   a communication circuit coupled to the controller and configured to communicate information with an external device,
   wherein the correlation circuit is configured to receive a value for the fixed correlation threshold from the external device and to initialize the device-variable correlation threshold with the received fixed correlation threshold value.

6. The apparatus of claim 4, wherein the cardiac signal sensing circuit includes at least one implantable electrode configured to sense an electrical cardiac signal in an atrium and at least one implantable electrode configured to sense an electrical cardiac signal in a ventricle, and wherein the tachyarrhythmia detection circuit is configured for determining that the detected rhythm with elevated ventricular rate is not ST if at least one of the following conditions is true:
   a measured increase in heart rate exceeds a specified heart rate threshold within a specified time period;
   a P-wave to R-wave (PR) interval changes from a baseline P-R interval value by at least a specified threshold value within a specified time period; and
   an increase in a ventricular contraction (V) rate that exceeds an atrial contraction (A) rate within a specified time period.

7. The apparatus of claim 4, wherein the electrical cardiac signal sensing circuit includes at least one implantable electrode configured to sense an electrical cardiac signal in an atrium and at least one implantable electrode configured to sense an electrical cardiac signal in a ventricle, and wherein the tachyarrhythmia detection circuit is configured for determining that the detected rhythm with elevated ventricular rate is not ST if a measured increase in heart rate exceeds a specified heart rate threshold within a specified time period.

8. The apparatus of claim 1, wherein the cardiac signal sensing circuit includes at least one implantable electrode configured to sense an electrical cardiac signal in an atrium and at least one implantable electrode configured to sense an electrical cardiac signal in a ventricle,
   wherein the tachyarrhythmia detection circuit is configured for deeming the detected rhythm with elevated ventricular rate as atrial tachyarrhythmia, and wherein the correlation circuit is configured to:
      compare the calculated correlation to a fixed correlation threshold, before the comparison to the device-variable correlation threshold, to determine whether the detected rhythm is correlated to the template; and
      replace the comparison to the fixed correlation threshold with the comparison to the device-variable correlation threshold while the detected rhythm with elevated ventricular rate is deemed an atrial tachyarrhythmia when the detected rhythm correlated to the template and the device-variable correlation threshold is lower than the fixed threshold; and
   wherein the therapy circuit is configured to inhibit the VT therapy while the detected rhythm is deemed an atrial tachyarrhythmia, and when the detected rhythm correlates to the template according to the comparison of the calculated correlation to the device-variable correlation threshold.

9. The apparatus of claim 8, wherein the tachyarrhythmia detection circuit is configured to deem the rhythm with elevated ventricular rate as atrial tachyarrhythmia if at least one of following conditions is true:
   an atrial contraction rate exceeds a specified atrial rate threshold and an ventricular contraction rate is unstable; and the atrial contraction rate exceeds the ventricular contraction rate by a specified rate threshold.

10. The apparatus of claim 1, wherein the tachyarrhythmia detection circuit is configured to detect a normal sinus rhythm (NSR),
wherein the cardiac signal sensing circuit includes:
a rate channel sensing circuit configured to be coupled to at least one implantable heart rate sensing electrode; and
a second sensing circuit configured to be coupled to at least a second sensing electrode,
wherein the controller includes a template generator circuit configured for generating the template using a first signal sensed using the rate channel sensing circuit during an NSR, and a second signal sensed using the second sensing circuit during the NSR, the template including a fiducial point on the first sensed signal and correlation features on the second sensed signal; and
wherein the correlation circuit is configured for:
identifying a first fiducial position in a third signal sensed during using the rate channel sensing circuit during the detected rhythm with elevated rate;
aligning the template correlation features and correlation features of a fourth signal using the first fiducial position, wherein the fourth signal is sensed at the same time as the third signal using the second sensing circuit; and
calculating the correlation using the template correlation features and correlation features of the fourth signal.

11. The apparatus of claim 10, wherein the correlation circuit is configured for:
choosing a second fiducial position in the third signal that is shifted from the first fiducial position by at least one sample and re-aligning the correlation features of the fourth signal using the second fiducial position;
re-calculating the correlation using the correlation features of the fourth signal; and
determining whether the detected rhythm with elevated ventricular rate correlates to the contraindicated tachyarrhythmia using a maximum calculated correlation.

12. The apparatus of claim 11, wherein the correlation circuit is configured to replace the first fiducial position with the second fiducial position when the re-aligning using the correlation features of the second fiducial position yields the maximum calculated correlation during a plurality of correlations calculated during the detected rhythm with elevated ventricular rate.

13. The apparatus of claim 10, wherein the correlation circuit is configured to:
choose a second fiducial position in the third signal that is earlier than the first fiducial position by at least one sample and re-aligning the correlation features of the fourth signal using the second fiducial position;
calculate a second correlation using the template correlation features and the correlation features of the fourth signal;
choose a third fiducial position in the third signal that is later than the first fiducial position by at least one sample and re-aligning the correlation features of the fourth signal using the second fiducial position;
calculate a third correlation using the template correlation features and the correlation features of the fourth signal; and
determine whether the detected rhythm with elevated ventricular rate correlates to the template using a maximum calculated correlation.

14. The apparatus of claim 13, wherein the correlation circuit is configured to:
iteratively choose the second and third fiducial points by shifting at least one of earlier and later from the first fiducial point and re-align the correlation features;
calculate the correlations at the fiducial points to find the maximum calculated correlation;
replace the first fiducial point with the fiducial point corresponding to the maximum calculated correlation.

15. The apparatus of claim 10, wherein the template generator circuit is configured to:
determine the fiducial point on the first sensed signal;
select a plurality of correlation features on the second sensed signal, wherein selecting a feature includes determining a feature amplitude and a time of the feature relative to the fiducial point; and
store the correlation features and relative times in the memory for tachyarrhythmia classification.

16. The apparatus of claim 10, wherein the second sensing circuit includes at least one implantable shock electrode.

17. The apparatus of claim 1, wherein the apparatus is a single chamber implantable device,
wherein the cardiac signal sensing circuit includes at least one implantable electrode configured to sense an electrical cardiac signal in a ventricle,
wherein the tachyarrhythmia detection circuit is configured for deeming the detected rhythm with elevated ventricular rate as atrial tachyarrhythmia if a ventricular contraction rate is unstable, and wherein the correlation circuit is configured to:
compare the calculated correlation to a fixed correlation threshold, before the comparison to the device-variable correlation threshold, to determine whether the detected rhythm is correlated to the template; and
replace the comparison to the fixed correlation threshold with the comparison to the device-variable correlation threshold while the detected rhythm with elevated ventricular rate is deemed an atrial tachyarrhythmia when the detected rhythm correlated to the template and the device-variable correlation threshold is lower than the fixed threshold; and
wherein the therapy circuit is configured to inhibit the VT therapy while the detected rhythm is deemed an atrial tachyarrhythmia, and when the detected rhythm correlates to the template according to the comparison of the calculated correlation to the device-variable correlation threshold.

18. A method comprising:
sensing an electrical cardiac signal;
detecting a rhythm with elevated ventricular rate from the cardiac signal;
calculating a value of correlation between the electrical cardiac signal of the detected rhythm and a template;
comparing the calculated correlation value to a device-variable correlation threshold to determine whether the detected rhythm correlates to a tachyarrhythmia for which a ventricular tachycardia (VT) therapy is contraindicated;
iteratively calculating the correlation value and comparing the calculated value to the device-variable correlation threshold; and
inhibiting the VT therapy while the detected rhythm with elevated ventricular rate correlates to the template according to the comparison of the calculated correlation value to the device-variable correlation threshold.

19. The method of claim 18, including recurrently updating the device-variable correlation threshold while the VT therapy is inhibited, the updating using a previous device-variable correlation threshold value and a current calculated correlation.

20. The method of claim 19, including beginning the updating of the variable threshold when a heart rate within a specified rate below a lowest VT rate zone is detected.

21. The method of claim 18, including:
comparing the calculated correlation value to a fixed correlation threshold before the comparison to the device-variable correlation threshold;
replacing the comparison of the calculated correlation value to the fixed correlation threshold with the comparison of the calculated correlation value to the device-variable correlation threshold while the detected rhythm is deemed a sinus tachycardia, when the detected rhythm is correlated to the template using the fixed correlation threshold, and when the device-variable correlation threshold is lower than the fixed correlation threshold; and
wherein the inhibiting the VT therapy includes inhibiting the VT therapy while the detected rhythm is deemed a sinus tachycardia and when the detected rhythm correlates to the template according to the comparison of the calculated correlation value to the device-variable correlation threshold.

22. The method of claim 21, including:
receiving a value for the fixed correlation threshold from an external device; and
initializing the device-variable correlation threshold with the received fixed correlation threshold value prior to adjustment of the device-variable correlation threshold.

23. The method of claim 21, including deeming that the detected rhythm with elevated ventricular rate is not sinus tachycardia if at least one of the following conditions is true:
a measured increase in heart rate exceeds a specified heart rate threshold within a specified time period;
a P-wave to R-wave (PR) interval changes from a baseline P-R interval value by at least a specified threshold value within a specified time period; and
an increase in a ventricular contraction (V) rate that exceeds an atrial contraction (A) rate within a specified time period.

24. The method of claim 18, wherein the detecting a rhythm with elevated ventricular rate includes detecting an atrial tachyarrhythmia, and wherein the method includes:
comparing the calculated correlation to a fixed correlation threshold, before the comparison to the device-variable correlation threshold, to determine whether the detected rhythm with elevated ventricular rate is correlated to a template;
replacing the comparison to the fixed correlation threshold with the comparison to the device-variable correlation threshold while the detected rhythm is deemed an atrial tachyarrhythmia, when the detected rhythm initially correlated to the template, and when the device-variable correlation threshold is lower than the fixed correlation threshold; and
inhibiting the VT therapy while the detected rhythm is deemed an atrial tachyarrhythmia, and when the detected rhythm correlates to the template according to the comparison of the calculated correlation to the device-variable correlation threshold.

25. The method of claim 24, including deeming that the detected rhythm with elevated ventricular rate is atrial tachyarrhythmia if at least one of the following conditions is true:
an atrial contraction rate exceeds a specified atrial rate threshold and an ventricular contraction rate is unstable; and
the atrial contraction rate exceeds the ventricular contraction rate by a specified rate threshold.

26. The method of claim 18, wherein calculating the correlation includes:
sensing a first electrical cardiac signal during a normal sinus rhythm (NSR) using at least one heart rate sensing electrode and sensing a second electrical cardiac signal during the NSR using at least a second sensing electrode;
generating a template using the first and second sensed cardiac signals, the template including a fiducial point on the first cardiac signal and correlation features on the second cardiac signal;
sensing a third electrical cardiac signal during the detected rhythm with the elevated ventricular rate using the rate sensing electrode and sensing a fourth electrical cardiac signal during the detected rhythm using the second sensing electrode;
identifying a first fiducial position in the third electrical cardiac signal and aligning the template correlation features and the correlation features of the fourth electrical cardiac signal using the first fiducial position; and
calculating the correlation using the correlation features of the template and the correlation features of the fourth electrical cardiac signal.

27. The method of claim 26, including:
choosing a second fiducial position on the third electrical cardiac signal that is shifted from the first fiducial position by at least one sample and re-aligning the correlation features of the fourth electrical cardiac signal using the second fiducial position;
re-calculating the correlation using the correlation features of the template and the correlation features of the fourth electrical cardiac signal; and
determining whether the detected rhythm with elevated rate correlates to the template using a maximum calculated correlation.

28. The method of claim 26, including replacing the first fiducial position with the second fiducial position when the re-aligning using the correlation features of the second fiducial position yields the maximum calculated correlation during a plurality of correlations calculated during the detected rhythm with elevated ventricular rate.

29. The method of claim 26, including:
choosing a second fiducial position on the third electrical cardiac signal that is earlier than the first fiducial position by at least one sample and re-aligning the correlation features of the fourth electrical cardiac signal using the second fiducial position;
calculating a second correlation using the correlation features of the template and the correlation features of the fourth electrical cardiac signal;
choosing a third fiducial position on the third electrical cardiac signal that is later than the first fiducial position by at least one sample and re-aligning the correlation features of the fourth electrical cardiac signal using the third fiducial position;
calculating a third correlation using the correlation features of the template and the correlation features of the fourth electrical cardiac signal; and
determining whether the detected rhythm with elevated ventricular rate correlates to the contraindicated tachyarrhythmia using a maximum calculated correlation.

30. The method of claim 29, including:
iteratively choosing the second and third fiducial points by shifting at least one of earlier and later from the first fiducial point and re-aligning the correlation features;
calculating the correlations at the fiducial points to find the maximum calculated correlation; and
replacing the first fiducial point with the fiducial point corresponding to the maximum calculated correlation.

31. The method of claim 30, wherein replacing includes replacing the first fiducial point with the fiducial point having the most maximum calculated correlations every N cardiac cycles, wherein N is an integer.

32. The method of claim 26, wherein generating a template includes:
determining a fiducial point on the first electrical cardiac signal sensed using the rate sensing electrode;
selecting a plurality of correlation features on the second electrical cardiac signal sensed using the shock channel, wherein selecting a correlation feature includes selecting a feature amplitude and time relative to the fiducial point; and
storing the correlation features for tachyarrhythmia classification.

33. An apparatus comprising:
means for sensing an electrical cardiac signal;
means for detecting a detected rhythm with elevated ventricular rate from the signal;
means for calculating a correlation value between an electrical cardiac signal of the detected rhythm with elevated ventricular rate and a template;
means for comparing the calculated correlation to a device-variable correlation threshold to determine whether the detected rhythm with elevated ventricular rate correlates to a tachyarrhythmia for which a VT therapy is contraindicated; and
means for iteratively calculating the correlation value and inhibiting the VT therapy while the detected rhythm correlates to the template according to a comparison of the calculated correlation value to the device-variable correlation threshold.

* * * * *